United States Patent [19]

Rose

[11] Patent Number: 5,854,070
[45] Date of Patent: Dec. 29, 1998

[54] MURINE AND HUMANIZER 23F2G ANTIBODIES AND CELL LINES EXPRESSING SAID ANTIBODIES

[75] Inventor: Lynn M. Rose, Seattle, Wash.

[73] Assignees: ICOS Corporation, Bothell; Board of Regents of the University of Washington, Seattle, both of Wash.

[21] Appl. No.: 785,571

[22] Filed: Jan. 21, 1997

Related U.S. Application Data

[63] Continuation of Ser. No. 396,089, Feb. 28, 1995, abandoned, which is a continuation of Ser. No. 94,535, Jul. 16, 1993, abandoned, which is a continuation-in-part of Ser. No. 60,699, May 10, 1993, abandoned, which is a continuation of Ser. No. 915,068, Jul. 16, 1992, abandoned.

[51] Int. Cl.$^6$ .......................... C07K 16/18; C07K 16/28; C12N 5/12

[52] U.S. Cl. .................. 435/343.2; 435/343; 435/343.1; 435/326; 435/328; 435/346; 435/358; 435/334; 530/387.1; 530/387.3; 530/388.1; 530/388.2; 530/388.22; 530/388.7; 530/388.73; 530/388.75

[58] Field of Search .............................. 435/70.21, 172.2, 435/334, 343.2; 530/387.1, 388.2, 388.73

[56] References Cited

U.S. PATENT DOCUMENTS 4,797,277  1/1989  Arfors .

FOREIGN PATENT DOCUMENTS

| 440 351 A2 | 8/1992 | European Pat. Off. . |
| WO 92/03473 | 3/1992 | WIPO . |
| WO 92/04034 | 3/1992 | WIPO . |
| WO 92/06697 | 4/1992 | WIPO . |
| WO 93/02191 | 2/1993 | WIPO . |

OTHER PUBLICATIONS

Alvord, JC Koetsier, editor; "Disseminated Encephalomyelitis: Its Variations in Form and Their Relationships to Other Diseases of the Nervous System", *Handbook of Clinical Neurol.*, 3(47):467–502, Koetsier (ed.); Amsterdam; Elsevier Science Publishers BV (1985).

Arfors et al., "A Monoclonal Antibody to the Membrane Glycoprotein Complex CD18 Inhibits Polymorphonuclear Luekocyte Accumulation and Plasma Leakage In Vivo", *Bloo*, 60:338–340 (1987).

Beatty et al., "Definition of a Common Leukocyte Cell–Surface Antigen (Lp95–150) Associated with Diverse Cell–Mediated Immune Functions," *J. Immunol.*, 131:2913–2918 (1983).

Bohnsack et al., "Human Neutrophil Adherence to Laminin In Vitro", *J. Exp. Med.*, 171:1221–1237 (1990).

Cannella et al., "Anti–Adhesion Molecule Therapy in Experimental Autoimmune Encephalomyelitis (EAE)", *J. Neuropathol. Exp. Neurol.*, 51:382 (May 1992).

Carter et al., "Humanization of an Anti–p185$^{HER2}$ Antibody for Human Cancer Therapy", *Proc. Nat'l Acad. Sci.(USA)*, 89:4285–4289 (1992).

Co et al., "Chimeric and Humanized Antibodies with Specificity for the CD33 Antigen$^1$ ̈ *J. Immunol.*, 148:1149–1154 (1992).

Co et al., "Humanized Antibodies for Antiviral Therapy", *Proc. Nat'l. Acad. Sci. (USA)*, 88:2869–2873 (1991).

Doerschuk et al., "CD18–Dependent and –Independent Mechanisms of Neutrophil Emigration in the Pulmonary and Systemic Microcirculation of Rabbits", *J. Immunol.*, 144:2327–2333 (1990).

Goding, *Monoclonal Antibodies: Principles and Practice*, 2d Ed., pp. 241–280, Academic Press, New York (1986).

Gorman et al., "Reshaping a Therapeutic CD4 Antibody", *Proc. Nat'l Acad. Sci. (USA)*, 88:4181–4185 (1991).

Harlan et al., "The Role of Neutrophil Membrane Glycoprotein GP–150 in Neutrophil Adherene to Endothelium In Vitro", *Blook*, 66:167–178 (1985).

Hauser et al., "Immunoregulatory T–Cells and Lymphocytotoxic Antibodies in Active Multiple Sclerosis: Weekly Analysis Over a Six–Month Period", *Ann Neurol.*, 13:418–425 (1983).

Hernandez et al., "Role of Neutrophils in Ischemia–Reperfusion–Induced Microvascular Injury", *Am. J. Physiol.*, 253:H699 (1987).

Hildreth et al., "Involvement of a Leukocyte Adhesion Receptor (LFA–1) in HIV–Induced Suncytium Formation", *Science*, 244:1075–1083 (1989).

Hynes, "Integrins: A Family of Cell Surface Receptors", *Cell*, 48:549–554 (1987).

Jutila et al., "Inflammation–Induced Endothelial Cell Adhesion to Lymphocytes, Neutrophils, and Monocytes", *Transplantation*, 48:727–731 (1989).

Kettleborough et al., "Humanization of a Mouse Monoclonal Antibody by CDR–grafting: The Improtance of Framework Residues on Loop Conformation", *Protein Engineering*, 4(7):773–783 (1991).

Kil, "Block–Face Application of a 7:3 Propylene Glycol–Water Mixture to facilitate Cutting of Large Frozen Sections", *Stain Technology*, 47:271 (1972).

Kirkham et al., "Immunoglobulin $V_H$ clan and family identity predicts variable domain structure and may influence antigen binding", *EMBO J.*, 11:603–609 (1992).

Luscinskas et al., "Endothelial–Leukocyte Adhesion Molecule–1 Dependent and Leukocyte (CD11/CD18)–Dependent Mechanisms Contribute to Polymorphonuclear Leukocyte Adhesion to Cytokine–Activated Human Vascular Endothelium", *J. Immunol.*, 142:2257–2263 (1989).

(List continued on next page.)

*Primary Examiner*—Lila Feisee
*Assistant Examiner*—Phillip Gambel
*Attorney, Agent, or Firm*—Marshall, O'Toole, Gerstein, Murray & Borun

[57] ABSTRACT

Disclosed are methods for the alleviation of symptoms associated with inflammatory disease states, and more particularly to the inhibition of inflammatory processes associated with the multiple sclerosis disease, by administering a pharmaceutically effective amount of antibody substance immunologically reactive with the common β chain (CD18) of human leukocyte integrins and/or competes with mAb 60.3 for binding to human LFA-1.

6 Claims, 7 Drawing Sheets

OTHER PUBLICATIONS

Maeda et al., "Construction of Reshaped Human Antibodies with HIV–Neutralizing Activity", *Hum. Antibod. Hybridomas*, 2:124–134 (1991).

Price et al., "In Vivo Inhibition of Neutrophil Function in the Rabbit Using Monoclonal Antibody to CD18", *J. Immunol.*, 139:4174–4177 (1987).

Prineas et al., "Macrphages, Lymphocytes, and Plasma Cells in the Perivascular Compartment in Chronic Multiple Sclerosis", *Lab. Invest.*, 38:409–421 (1978).

Queen et al., "A Humanized Antibody That Binds to the Interleukin 2 Receptor", *Proc. Nat'l Acad. Sci.* (USA), 86:10029–10033 (1989).

Racke et al., "Modification of Experimental Allergic Encephalomyelitis by Administration of Antibodies", *Journal of Cellular Biochemistry*, 17A:355 (1993).

Raine et al., "Homing to Central Nervous System Vasculature by Antigen–Specific Lymphocytes", *Lab Investigations*, 63(4):476–489 (1990).

Rose et al., "In Vivo Administration of Anti–CD4 Monoclonal Antibody Prolongs Survival in Longtailed Macaques with Experimental Allergic Encephalomyelities", *Clin. Immunol. Immunopathol.*, 45:405–423 (1987).

Rose et al., "Magnetic Resonance Imaging and Peripheral Blood Abnormalities in Experimental Allergic Encephalomyelities", *Biomed. and Pharmacother.*, 43:347–353 (1989).

Rose et al., "Remitting–Relapsing EAE in Nonhuman Primates: A Valid Model of Multiple Sclerosis", *Clin. Immunol. Immunopathol.*, 59:1–15 (1991).

Rose et al., "Fluctuations of T–and B–Cell Subsets in Basic Protein–Induced Experimental Allergic Encephalomyelitis (EAE) in Long–Tailed Macaques", *Clin. Immunol. Immunopathol.*, 44:93–106 (1987).

Sanchez–Madrid et al., "Mapping of Antigenic and Functional Epitopes on the α–and β–Subunits of Two Related Mouse Glycoproteins Involved in Cell Interactions LFA–1 and MAC–1*", *J. Exp. Med.*, 158:586–602 (1983).

Sanchez–Madrid et al., "A Human Leukocyte Differentiation Antigen Family with Distinct α–Subunits and a Common β–Subunit: The Lymphocyte Function–Associated Antigen (LFA–1), the C3bi Complement Receptor (OKMI/Mac–1), and the p150,95 Molecule", *J. Exp. Med.*, 158:1785–1803 (1983).

Shaw et al., "Chronic Remitting–Relapsing Experimental Allergic Encephalomyelitis Induced in Monkeys with Homologous Myelin Basic Protein", *Ann Neurol.*, 24:738–748 (1988).

Shaw et al., *"Treatment of Experimental Allergic Encephalomyelitis in Monkeys", International Symposium on the Aetiology and Pathogenesis of the Demyelinating Diseases*, Sep. 1973, Kyoto.

Simonsen and Levinson, "Isolation and expression of an altered mouse dihydrofolate reductase cDNA", *Proc. Nat'l. Acad. Sci. USA*, 80:2495–2499 (1983).

Snyderman et al., "Molecular and Cellular Mechanisms of Leukocyte Chemotaxis", *Science*, 213:830–837 (1981).

Springer et al., "Adhesion Receptors of the Immune System", *Nature*, 346:425–434 (1990).

Tempest et al., "Reshaping a Human Monoclonal Antibody to Inhibit Human Respiratory Syncytial Virus Infection In Vivo", *Bio/Technology*, 9:266–271 (1991).

Thomas et al., "Differential Effects of Intravenous Anaesthetic Agents on Cell–Mediated Immunity in the Rhesus Monkey", *Clin. Exp. Immunol.*, 47:457–466 (1982).

Traugott et al., "Chronic Relapsing Experimental Allergic Encephalomyelitis: Identification and Dynamics of T and B Cells Within the Central Nervous System", *Cell. Immunol.*, 68:261–275 (1982).

Urlaub et al., "Isolation of Chinese Hamster Cell Mutants Deficient in Dihydrofolate reductase activity," *Proc. Nat'l Acad. Sci. USA*, 77:4216–4220 (1980).

Urlaub et al., "Deletion of the Diploid Dihydrofolate Reductase Locus from Cultured Mammalian Cells", *Cell*, 33:405–412 (1983).

Vedder et al., "A Monoclonal Antibody to the Adherence–Promoting Leukocyte Glycoprotein, CD18, Reduces Organ Injury and Improves Survival from Hemorrhagic Shock and Resuscitation in Rabbits", *J. Clin. Investo.*, 81:939 (1988).

Wall et al., "Effects of Ketamine Anaesthesia, Stress and Repeated Bleeding on the Haematology of Vervet Monkeys", *Lab Animals*, 19:138–144 (1985).

Weiner, Howard L. M.D. et al., "Immunotherapy of Multiple Sclerosis", *Ann Neurol.*, 23:211–222 (1988).

Welsh et al., "Augmentation of Adoptively Transferred Experimental Allergic Encephalomyelitis by Administration of a Monoclonal Antibody Specific for LFA–1α", *J. Neuroimmunology*, 43:161–168 (1993).

Wright et al., "Identification of the C3bi Receptor of Human Monocytes and Macrophages by Using Monoclonal Antibodies", *Proc. Nat'l. Acad. Sci.* (*USA*), 80:5699–5703 (1983).

Zimmerman et al., "Neutrophil Adherence to Human Endothelium In Vitro Occurs by CDw18 (Mol, MAC–1/LFA–1/GP 150,95) Glycoprotein–dependent and –independent Mechanisms", *J. Clin. Invest.*, 81:531–537 (1988).

Page et al. Biotechnology vol. 9 p. 64 1991.

Beatty et al, Journal of Immunology 131(6) p. 2913, 1983.

Wright et al. PNAS. 80 p. 5699, 1983.

Daugherty et al. Nucleic Acids Res. 19(9) 2471, 1991.

Harris et al. TibTeh. vol. 11 p. 42 1993

Hird et al. Genes and Larcuk Sikova eds. 183, 1990.

MURINE AND HUMANIZER 23F2G ANTIBODIES AND CELL LINES EXPRESSING SAID ANTIBODIES

This is a Rule 62 continuation of U.S. patent application Ser. No. 08/396,089 filed Feb. 28, 1995, now abandoned, which is a continuation of Ser. No. 08/094,535, filed Jul. 16, 1993, now abandoned, which in turn is a continuation-in-part of U.S. patent application Ser. No. 08/060,699, filed May 10, 1993, now abandoned, which in turn is a Rule 62 continuation of U.S. patent application Ser. No. 07/915,068, filed Jul. 16, 1992, now abandoned.

BACKGROUND OF THE INVENTION

The present invention relates generally to methods for the alleviation of symptoms associated with inflammatory disease states, and more particularly to the inhibition of inflammatory processes involved in the multiple sclerosis disease state through administration of a pharmaceutically effective amount of an antibody substance immunologically reactive with molecules expressed on the surface of leukocytes.

Inflammation is a body process central to a number of diseases and is the body's primary defense against infection. The inflammatory process involves an orchestrated series of events initiated in response to tissue damage. In all cases, this cellular damage ultimately leads to the influx of white blood cells (leukocytes) to the site of injury. As leukocytes arrive at the site of injury, they become metabolically activated and begin to secrete specific proteins (mediators) that are generally of defensive significance, for example, in the eradication of bacteria.

If unregulated, the inflammatory state may persist as a condition known as chronic inflammation. In this setting, the mediators produced may amplify the inflammatory response and cause damage to otherwise normal tissue. Depending upon the body site, such tissue damage may result in chronic diseases such as arthritis, multiple sclerosis, asthma, emphysema, ulcerative colitis, and various autoimmune diseases.

Multiple sclerosis (MS) is a chronic disease characterized by recurrent attacks of neurologic dysfunction due to lesions in the central nervous system. These lesions, termed "plaques," represent areas of axonal demyelination which are the hallmark of multiple sclerosis. The lesions contain inflammatory cells such as lymphocytes, macrophages and neutrophils in areas where myelin is being destroyed. The classic clinical features of multiple sclerosis include impaired vision and weakness or paralysis of one or more limbs. After a number of years, patients experience a slow, steady deterioration of neurologic function. The disease course is unpredictable and involves exacerbations and remissions in 75% of patients. Although a few patients die within the first few years of onset, the average duration of disease is greater than 30 years.

There are an estimated 250,000 cases of multiple sclerosis in the United States, with approximately 10,000 new cases occurring each year. The cause is unknown but epidemiology implicates immunologic or infectious factors resulting in a chronic inflammatory brain condition. Multiple sclerosis is a disease of young adults, with 66% of cases occurring at ages 20–40; 60% of the patients are women. Over one million physician visits occur annually for multiple sclerosis in the United States alone; however, there is currently no effective treatment for multiple sclerosis. Therapy is directed toward the reduction of the severity of acute episodes and prevention of relapses. In acute flare-ups, steroids reduce severity and speed recovery. Experimental therapy with other immunosuppressive agents, such as cyclophosphamide, has been tried, but with limited success.

A model for human multiple sclerosis is experimental allergic encephalomyelitis (EAE), an acute inflammatory and demyelinating disease of the central nervous system (CNS). [Rose, et al., *Clin. Immunol. Immunopathol.*, 59:1–15 (1991)]. For both EAE and MS, there is considerable evidence that immunological and inflammatory processes contribute to the pathogenesis of the disease. [Hauser, et al., *Ann Neurol* 13:418–425 (1983); Traugott, et al., *Cell. Immunol.*, 68:261–275 (1982); Rose, et al., *Clin. Immunol. Immunopathol.*, 45:405–423 (1987). This is supported by the presence of perivascular mononuclear cellular infiltrates in lesions and macrophage-dependent phagocytosis of myelin in the CNS white matter. [Prineas, et al., *Lab. Invest.*, 38:409–421 (1978); Alvord, J. C. Koetsier, editor; *Handbook of Clinical Neurol*, 3(47):467–502, Koetsier (ed.); Amsterdam; Elsevier Science Publishers BV (1985)]. The mechanisms by which these blood cells first recognize the brain as a target organ and then traverse the blood brain barrier are not well understood.

The migration of blood cells into extravascular sites of inflammation involves a complex series of events including: i) recognition of an intravascular chemotactic stimulus, ii) adherence to endothelium, iii) diapedesis across the endothelium, and iv) migration through subendothelial connective tissue. [Snyderman, et al., *Science*, 213:830–837 (1981)]. Endothelial cells (EC) found on lumenal surfaces of blood vessels are the first cells that leukocytes encounter during migration from the blood to the extravascular space. Molecules expressed by both the leukocytes and by the endothelial cells are important in regulating the adhesive interaction between these two cell types.

One family of leukocyte receptors, variously designated "leukocyte integrins," "leukointegrins," and "CD11/CD18 integrins," are involved in cell-cell and cell-protein interactions of all leukocytes. [Hynes, *Cell*, 48:549–554 (1987); Beatty, et al., *J. Immunol.*, 131:2913–2918 (1983)]. The CD11/CD18 antigen family consists of three heterodimers, each containing a unique α-chain (CD11a, CD11b, or CD11c), and a common β-chain (CD18). [Sanchez-Madrid, et al., *J. Exp. Med.*, 158:1785–1803 (1983)]. The CD11a/CD18 integrin is referred to as LFA-1; the CD11b/CD18 integrin is referred to as Mac-1; the CD11c/CD18 integrin is referred to as p 150,95.

Numerous murine hybridomas have been generated which produce monoclonal antibodies of varying isotype to the common β chain (CD18) of the leukocyte integrins. These include: mAb 1B4 [IgG2a; Wright, et al., *Proc. Nat'l. Acad. Sci. U.S.A.*, 80:5699–5703 (1983)]; mAb 60.3 [IgG2a; Beatty, et al., *J. Immunol.*, 131:2913–2918 (1983)]; mAb TS1/18 [IgG1; Sanchez-Madrid, supra]; mAb H52 [Hildreth, et al., *Science* 244:1075–1803 (1989)]; and ATCC T1B 218 [IgG2a Kappa; Springer, et al., *J. Exp. Med.*, 158:586–602 (1983)]. Production of chimeric and humanized monoclonal antibodies against human CD18 is referred to in Law, et al., European Patent Application 440 351 A2, published Aug. 7, 1992.

Monoclonal antibodies directed against the common β-chain of leukocyte integrins completely inhibit adherence of PMNCs to un-activated endothelial cells and certain matrix proteins in vitro. [Harlan, et al., *Blood*, 66:167–178 (1985); Zimmerman, et al., *J. Clin. Invest.*, 81:531–537 (1988); Bohnsack, et al., *J. Exp. Med.*, 171:1221–1237 (1990); Luscinskas, et al., *J. Immunol.*, 142:2257–2263

(1989)]. Moreover, the systemic administration of anti-CD11/CD18 antibodies inhibits tissue accumulation of PMNCs. [Springer, et al., *Nature*, 346:425–434 (1990); Jutila, et al., *Transplantation*, 48:727–731 (1989); Arfors, et al., *Blood*, 60:338–340 (1987); Price, et al., *J. Immunol.*, 139:4174–4177 (1987); and, Doerschuk, et al., *J. Immunol.*, 144:–2327–2333 (1990)].

Arfors, et al., supra, studied the effect of the anti-CD18 antibody, mAb 60.3, on induced PMN accumulation in vivo and found that both PMN accumulation and PMN-dependent plasma leakage were abolished in the inflammatory skin lesions of rabbits treated with mAb 60.3 prior to intra dermal injection with the chemotactic factors FMLP, leukotriene ($LTB_4$) and C5a. These chemotactic agents cause a significant increase in albumin extravasation; extravasation of PMNs at chemotaxin-injective sites is followed by plasma leakage. Curiously, histamine-induced PMN-independent plasma leakage was unaffected by pre-treatment with mAb 60.3.

Hernandez, et al., *Am. J. Physiol.*, 253:H699 (1987) investigated whether PMNs mediate the increase in microvascular permeability produced by ischemia-reperfusion (I/R) by treating cats with either saline, anti-neutrophil serum (ANS), or mAb 60.3. The results indicated that both PMN depletion and prevention of PMN adherence significantly attenuated the increase in microvascular permeability induced by I/R and that prevention of neutrophil adherence with mAb 60.3 afforded protection against I/R-induced microvascular injury. See also, U.S. Pat. No. 4,797,277. Similarly, Vedder, et al., *J. Clin. Invest.*, 81:939 (1988) concluded that increased leukocyte adhesiveness plays an important role in the development of multiple organ injury and death after general ischemia-reperfusion and that this injury may be significantly reduced by blocking leukocyte adherence functions with the mAb 60.3. Their results, however, did not rule out the possibility that other leukocytes or other leukocyte adherence functions may also be involved, as CD18 is present on all leukocytes.

Doerschuk, et al., supra, reported on the differential effects of mAb 60.3 on neutrophil (PMN) migration to either pulmonary or peritoneal sites of inflammation in rabbits. Inflammation in the abdominal wall of rabbits was induced following implantation of polyvinyl sponges containing one of the following stimuli: *Streptococcus pneumoniae*, endotoxin (*E. coli*), hydrochloric acid or phorbol myristate acetate (PMA). Peritoneal inflammation was induced by instillation of *S. pneumoniae* and pulmonary inflammation was induced by instilling intrabronchially either *S. pneumoniae*, hydrochloric acid, *E. coli* endotoxin, or PMA. Rabbits were pre-treated with either intra venous injection of mAb 60.3 or saline 20 minutes prior to initiating inflammation. The results demonstrated that mAb 60.3 inhibited PMN emigration in response to *S. pneumoniae*, hydrochloric acid, *E. coli* endotoxin, or PMA into both the abdominal wall and the peritoneal cavity. However, in the same animals, mAb 60.3 did not alter PMN emigration into the alveolar space, visceral pleura, or bronchial epithelium in response to *S. pneumoniae* or hydrochloric acid. In contrast, mAb 60.3 markedly inhibited PMN emigration into the alveolar space in response to *E. coli* endotoxin and abolished lung emigration in response to PMA. The results demonstrated that there are as yet unidentified organ-specific and stimulus-specific differences in PMN adherence mechanisms that could be due to differences in response of pulmonary and systemic endothelium to identical stimuli or, to the site-specific production of secondary mediators that affect the PMN or endothelial cell.

In addition to U.S. Pat. No. 4,797,277, which addresses methods for reperfusion therapy with anti-leukocyte-integrin antibody preparations, a number of quite generalized proposals for therapeutic uses of such antibodies have recently been made. PCT WO 92/04034, published Mar. 19, 1992, generically proposes the use of anti-CD18 antibodies in the treatment of endotoxin shock. PCT WO 92/03473, published Mar. 5, 1992, proposes use of CD18 peptide fragments and antibodies thereto in the treatment of a "disease". European Patent Application No. 440 451, supra, illustrates usefulness of recombinant humanized anti-CD18 antibodies in the treatment of rabbit dermal inflammation but projects utility in treatment of inflammation in "lung, central nervous system, kidney, joints, endocardium, pericardium, eyes, ears, skin, gastrointestinal tract and urogenital systems." Although multiple sclerosis is proposed as one of many disease states which "may be responsive to recombinant human anti-CD18 antibody," no studies of the effect of such antibodies on any chronic inflammatory disease states are reported in the published European Patent Application.

With particular reference to MS, Raine et al., *Lab. Investigations*, 63)4:476–489 (1990) noted that a variety of adhesion molecules appear to be involved in the lymphocyte homing and cell triggering processes extant in the disease state. Raine et al. further noted that disruption of any of the involved ligand pairs [e.g., LFA-1/ICAM-1, CD-2/LFA-3, CD4/class II MHC (HLA-DR)] might lead to alterations in lymphocyte traffic, effector cell activation, or effector cell function. The same research group later reported, however, that while treatment of EAE mice with anti-ICAM-1 antibodies resulted in some reduction in the degree of inflammation, treatment with anti-LFA-1 antibodies was lethal at high doses and had no effect on CNS changes at lower doses. See, Cannella et al., *J. Neuropathol. Exp. Neurol.*, 51:382 (May, 1992). See also, Racke et al., *Journal of Cellular Biochemistry*, 17A:355 (1993) reporting that low doses of anti-ICAM-1 and anti-LFA-1 antibodies resulted in more severe disease in EAE mice, while higher doses appeared to delay disease onset and only treatment with both antibody preparations allowed observation of suppression of clinical signs; and Welsh et al., *J. Neuroimmunology*, 43:161–168 (1993) reporting that anti-LFA-1 antibody treatment augmented the severity of disease symptoms in adoptively transferred EAE.

There thus continues to exist a need in the art for therapeutic materials and regimens for the treatment of inflammation associated with multiple sclerosis.

BRIEF SUMMARY OF THE INVENTION

The present invention provides novel and effective methods for the treatment of inflammatory processes and the alleviation of symptoms associated with the multiple sclerosis disease state comprising administering a therapeutically effective amount of an anti-CD18 and/or anti-LFA-1 antibody substance. Alternatively stated, the present invention addresses the use of anti-CD 18 and/or anti-LFA-1antibodies for the manufacture of a medicament for alleviation of symptoms associated with the multiple sclerosis disease state.

Antibody substances useful in practice of the present invention include monoclonal and polyclonal antibodies, antibody fragments, single chain antibodies, chimeric and/or CDR-grafted (including humanized) antibodies and the like which are specifically immunoreactive with one or more epitopes presented by the common β-chain (CD18) of human leukocyte integrins. Antibodies may be of any class or subclass including IgG, IgA, IgD, IgE and/or IgM. Among the preferred antibodies for practice of the invention is mouse monoclonal antibody mAB 60.3 of the IgG2a isotype.

Also provided by the present invention are monoclonal anti-human CD18 antibodies produced by hybridoma cell lines designated 23F2G (A.T.C.C. HB 11081) 23I11B and 22F12C. Hybridoma cell line 23F2G was deposited with the American Type Culture Collection (A.T.C.C.) 12301 Parklawn Drive, Rockville, Md., 20852 on Jun. 30, 1992 and was assigned accession No. A.T.C.C. HB 11081. These and antibodies produced by hybridomas 22B3B and 22J4A are characterized as competitive inhibitors of the binding of mAb 60.3 to human LFA-1 on Hut78 cells. The 23F2G antibody produced by A.T.C.C. HB 11081 has correspondingly been "humanized" and transformed mammalian cells expressing humanized forms of the mouse 23F2G antibody were deposited with the A.T.T.C. on Jul. 9, 1993 and were assigned under accession Nos. A.T.C.C. CRL 11397 and CRL 11398 respectfully.

Other aspects and advantages of the present invention will be apparent upon consideration of the enclosed detailed description of embodiments thereof, reference being had to the drawing wherein:

FIGS. 1 and 2 present magnetic resonance images illustrating results of practice of the invention in the Experimental Allergic Encephalomyelitis (EAE) model system;

FIGS. 3 and 4A, 4B, 4C and 4D represent histological results of practice of the invention in the EAE model system; and FIG. 5 and 6 are schematic representations of expression vectors encoding humanized heavy and light chains, respectively, of an antibody of the invention.

DETAILED DESCRIPTION

Figure 1A:
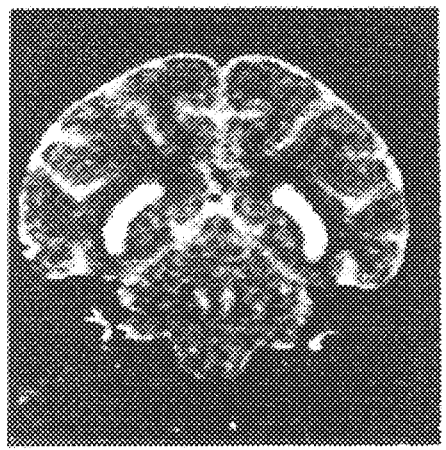
Figure 1B:
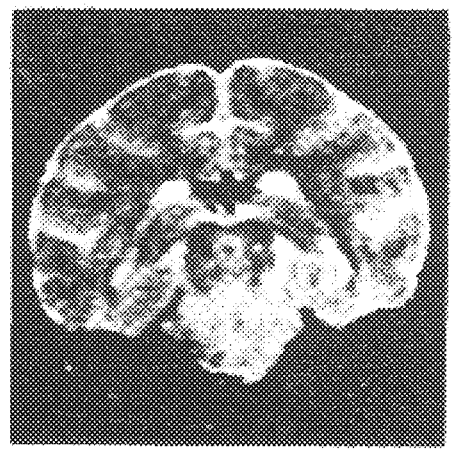
Figure 1C:
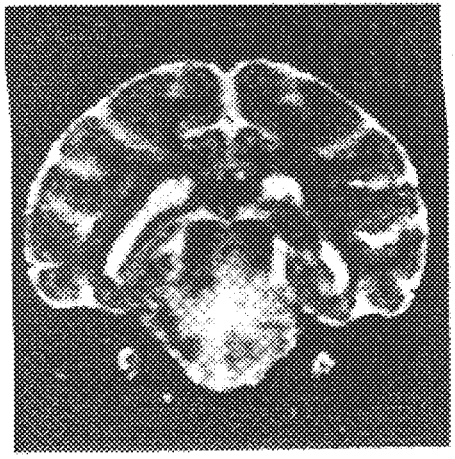
Figure 1D:
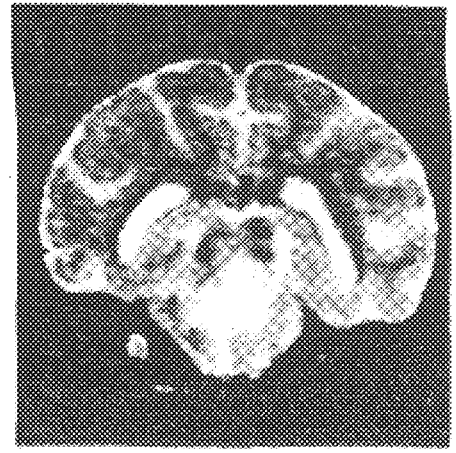
Figure 2A:
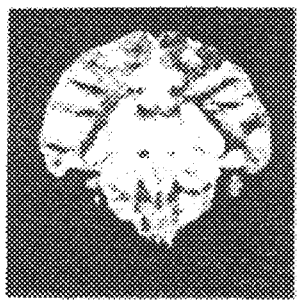
Figure 2B:
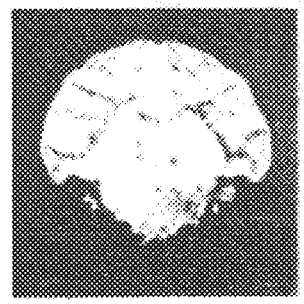
Figure 2C:
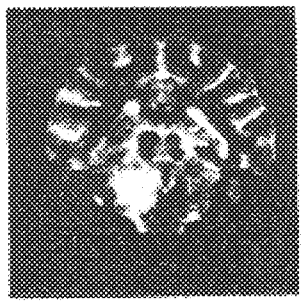
Figure 2D:
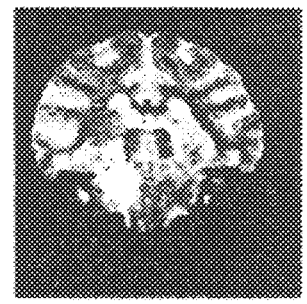
Figure 2E:
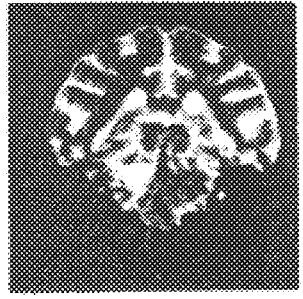
Figure 2F:
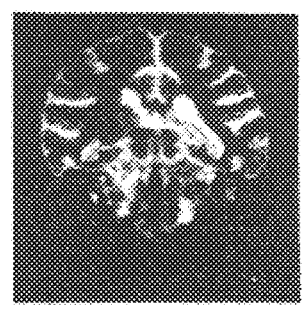
Figure 2G:
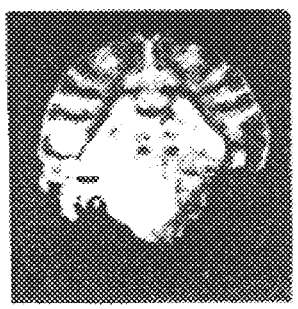

The following detailed description illustrates practice of the invention through use of the mouse monoclonal anti-CD18 antibody mAb 60.3, mouse monoclonal antibody 23F2G and humanized antibody 23F2G to alleviate progression of Experimental Allergic Encephalomyelitis (EAE) in macaque monkeys. Non-human primates induced to develop EAE, an acute inflammatory disease of the central nervous system and a model of the human disease MS, were chosen because of the many immunological and neuroplphysiological similarities EAE shares with MS (Rose, et al., supra.) and because the CD18 antigen recognized by mAb 60.3 is present in high density on monkey peripheral blood leukocytes (Rose, et al., *Clin. Immunol. Immunopathol.*, 44:93–106 (1987).

Example 1 relates to the induction of EAE in monkeys. Example 2 describes treatment by mAb 60.3 antibody infusion and Example 3 relates to the evaluation of disease progression as monitored by a combination of clinical evaluation, blood analysis, and magnetic resonance imaging, including immunocytochemical staining of frozen tissue sections obtained post-mortem. Example 4 describes the preparation of hybridoma cell lines producing anti-human CD18 antibodies and Example 5 relates use of monoclonal antibodies from hybridoma 23F2G in treatment of EAE. Example 6 addresses humanization of antibody 23F2G and Example 7 describes additional treatments of EAE macaque monkeys with antibody 23F2G and humanized 23F2G.

EXAMPLE 1

Induction of EAE

Eighteen male monkeys *Macaca fascicularis* weighing 2–3 kg were sensitized to myelin basic protein (BP) by the intra dermal injection of 0.1 ml of an emulsion containing 5.0 mg of monkey BP and 0.5 mg of heat-killed *M. tuberculosis*. Each animal was obtained and housed by the Regional Primate Research Center at the University of Washington, Seattle. The Primate Center conforms to the National Institutes of Health Guide for the Care and Use of Laboratory Animals. Ten days after sensitization to BP, each animal was outfitted with a femoral catheter and tether to facilitate blood sampling and the administration of treatments or anesthetics for magnetic resonance imaging (MRI). The animals were maintained on intravenous heparin (18 units/hour) to prevent blood clots from forming in the intra venous lines.

The animals were randomly admitted to specific treatment groups before they were sensitized to BP. This was done to schedule MRI and to prevent the severity of clinical signs at the onset from influencing the choice of therapy. Primate Center personnel, responsible for deciding when animals should be treated or sacrificed, were blinded regarding the treatment history of each animal. Table 1 below provides a statement of criteria for determination of clinical signs and grades of EAE in the animals.

TABLE 1

CLINICAL SIGNS AND GRADES OF EAE IN MACAQUES

| Score | Signs |
|---|---|
| ? | Prodromal signs, including weight loss, anorexia, yawning, slow response to stimuli, irritability |
| ± | Mild neurologic signs, including "headache" (acute distress), "apathy" (indifference), hypokinesia, drooling, clumsiness in using limbs, nystagmus |
| + | Moderate neurologic signs, including akinesia, blindness, ataxia, tremor, ptosis, seizures, paresis, incontinence |
| ++ | Severe neurologic signs including somnolence, paraplegia, hemiplegia, or quadriplegia |
| +++ | Moribund state with semicoma, coma, decerebration or decortication |
| D | Death |

EXAMPLE 2

Treatment By Antibody Infusion

At the onset of definite clinical signs (± to +) six EAE animals received a bolus injection of mAb 60.3 (2 mg/kg) and dexamethasone (4 mg/kg). Dexamethasone was administered to reduce the incidence of severe acute EAE which is rapidly fatal within 48 hours unless treated immediately. Severe acute EAE occurs in approximately 25% of animals induced to develop EAE and is caused by edema in areas involving or impinging upon the brain stem or cerebral cortex. Following injection of the bolus, these six animals were treated by continuous infusion of mAb 60.3 (2 mg/kg/day) for seven days. Over the seven day treatment period, the dose of dexamethasone, which started at 4 mg/kg, was halved every two days until only 1 mg had been in effect for three days. Six control EAE animals were treated only with dexamethasone, following the same protocol outlined above, and six additional controls were treated with continuous infusion of saline.

Animals that improved and/or stabilized as a result of therapy were sacrificed six weeks after the onset of clinical signs. Animals that experienced a clinical relapse (clinical signs ≧++) some time after the cessation of treatment and before six weeks had elapsed, were sacrificed shortly after the onset of the relapse. Animals that did not respond well to therapy and continued to deteriorate clinically (clinical signs ≧++) were sacrificed without completing the treatment program. The statistical significance of differences in survival times in each treatment group was determined by two-tailed Student t analysis.

EXAMPLE 3
Evaluation of Disease Progression

Disease progression was monitored by a combination of clinical evaluation, blood analysis and magnetic resonance imaging. Clinical evaluations were performed twice daily.

As indicated in Table 2 below, all of the animals in this study developed clinical signs of EAE 13–26 days after sensitization to myelin basic protein.

In Table 2, listing of animal numbers in boldface identified animals scanned by MRI; the Onset/Grade column reflects the day of onset after sensitization and the severity of clinical signs (see Table 1) at onset; the Survival/Grade column reflects days of survival post-onset and severity of clinical signs at time of sacrifice.

TABLE 2

THERAPEUTIC RESULTS

| Animals | Onset/Grade | Treatment | Survival/Grade |
|---------|-------------|-----------|----------------|
| 89070   | 17 days/+   | 60.3 + dex | 2 days/D      |
| 89075   | 21 days/+   | 60.3 + dex | 42 days/±     |
| 89080   | 21 days/+   | 60.3 + dex | 42 days/±     |
| 89069   | 18 days/±   | 60.3 + dex | 42 days/±     |
| 89071   | 18 days/±   | 60.3 + dex | 21 days/++    |
| 89074   | 22 days/+   | 60.3 + dex | 13 days/+     |
| 87143   | 21 days/±   | dex alone  | 17 days/++    |
| 87125   | 24 days/±   | dex alone  | 1 day/++      |
| 87209   | 21 days/±   | dex alone  | 2 days/++     |
| 89077   | 16 days/±   | dex alone  | 1 day/D       |
| 87200   | 22 days/±   | dex alone  | 13 days/++    |
| 87069   | 26 days/±   | dex alone  | 9 days/++     |
| 84228   | 13 days/+   | saline     | 5 days/D      |
| 84218   | 19 days/+   | saline     | 3 days/D      |
| 84291   | 25 days/+   | saline     | 1 day/D       |
| 86140   | 26 days/+   | saline     | 3 days/D      |
| 86187   | 19 days/+   | saline     | 1 day/++      |
| 87209   | 15 days/+   | saline     | 1 day/++      |

As indicated in Table 2, all eighteen animals developed clinical signs of EAE which ranged in severity from ± to + at the onset of disease. Six of the eighteen EAE animals (33%) died of severe acute EAE 1–5 days after onset. Four of the six had been treated with saline, one with dexamethasone, and one with a combination of dexamethasone and mAb 60.3. The remaining twelve animals were sacrificed at various times after onset either because they had deteriorated clinically or because they had completed the six-week post-treatment protocol.

Out of six mAb-treated animals, five either improved or stabilized with continuing, but not worsening, clinical signs. Animal 89071 improved, but suffered an acute relapse two weeks after the cessation of treatment and was sacrificed at 21 days. Animal 89074 was sacrificed at 13 days, one week after the cessation of treatment, to investigate an abnormal lipid signal detected by magnetic resonance spectroscopy (MRS), a technique being developed for studies of demyelination in the nonhuman primate [Richards et al., New York, Soc. Mag. Reson. Med. 2: p.1043 (1990)]. This animal had improved as a result of therapy and was clinically stable at the time of sacrifice. Animals 89075, 89080, and 89069 were all clinically stable six weeks after onset. The mean survival time of mAb 60.3-treated animals was 30 days. Control animals treated with saline (excluding animal 87220) survived 1–5 days after onset, with a mean survival time of 3 days. Animals treated with dexamethasone survived 1–17 days after onset, with a mean survival time of 7 days, 3 of 6 dying of their disease 1–2 days after onset, and 3 of 6 surviving 9,13 and 17 days, respectively, until they were sacrificed due to deteriorating clinical signs (≧++).

Magnetic Resonance Imaging

MRI was used to map the anatomic distribution of the lesions in all six of the mAb-treated EAE animals, two dexamethasone-treated animals, and two saline-treated animals. Conventional spin-warp imaging was performed using a General Electric CSI-II NMR imager/spectrometer (2 Tesla magnet) as described in Rose et al., Biomed. and Pharmacother., 43:347–353 (1989). Images were acquired once a week before the onset of clinical signs and twice a week after the onset of clinical signs. The animals were anesthetized with ketamine and positioned in the magnet so that the center of the brain was at magnet iso-center. Coronal T2-weighted images (TE=80 msec, TR=3000 msec) were used to find abnormal and normal brain regions. Lesions were detected in 60% of the scanned animals on or before the onset of clinical signs. Most lesions were localized in the cerebral white matter, optic tracts, visual radiations or brainstem. The lesions were identified as areas of increased brightness (white) in a T2-weighted MR image. Of the four control animals that were scanned, only one survived long enough to obtain post-treatment scans. In this dexamethasone-treated animal (87069) a brainstem lesion, detected one day before the onset of clinical signs, progressed in size and intensity until the animal was sacrificed nine days later as shown in FIG. 1. Plate A represents a "normal" brain scan, 21 days after sensitization; Plate B reveals detection of a brainstem lesion two days after onset of clinical signs i.e., 28 days post sensitization: Plates C and D illustrate gradual progression of the brainstem lesion 35 and 38 days after sensitization, respectively.

Following treatment with mAb 60.3, the MRI lesions detected in 5 of 6 animals diminished in both size and intensity. Three animals (89075, 89071, and 89074) had evidence of brainstem lesions at the onset of clinical signs. Although such lesions are frequently fatal if untreated [Shaw et al., Ann. Neurol. 24:738–748 (1988)], these lesions disappeared in all three animals following treatment with mAb 60.3. FIG. 2 demonstrates the progression of the brainstem lesion in animal 89071. In the Figure, Plate A illustrates a normal brain scan 15 days post sensitization; Plate B shows a brainstem lesion at the onset of clinical signs, i.e., 18 days after sensitization; Plates C through F illustrate gradual resolution of the brainstem lesion through antibody treatment as monitored at 22, 25, 29 and 32 days post sensitization; Plate G illustrates reappearance of a lesion in the same region which was accompanied by clinical relapse 39 days post sensitization and 14 days after cessation of treatment. Enlarging lesions are identified as prominent areas of increased intensity (white) on the scans. As noted above, two weeks after the treatment was discontinued, 89071 clinically relapsed and MR images demonstrated a larger, more intense lesion in the brainstem. The relapse was not treated and the animal was sacrificed.

Animal 89080 developed a major hemorrhagic lesion in the lateral geniculate nucleus and striatum. Hemorrhagic lesions are usually fatal and usually do not respond to treatment (Shaw et al., supra) but this lesion almost completely disappeared following administration of mAb 60.3. Animal 89069 had the mildest disease of any of the animals, as determined by MRI, with several small, but intense, sub-cortical white matter lesions that disappeared following treatment.

Two of the longest surviving animals (89080 and 89069) developed a chronic disease characterized by the appearance of new, smaller, MRI-detectable lesions 25 and 22 days, respectively, after the cessation of treatment. These secondary lesions were not as severe as the first lesions and were accompanied by milder clinical signs which were not treated. Animal 89074 was sacrificed 13 days after the onset of disease, to investigate an abnormal lipid signal detected by MRS. At the time of sacrifice, six days after stopping treatment, his initial lesions were gone, but a new smaller subclinical lesion had appeared on the opposite side of the brain. No new lesions were ever detected in animal 89075 after cessation of treatment.

Figure 3A:
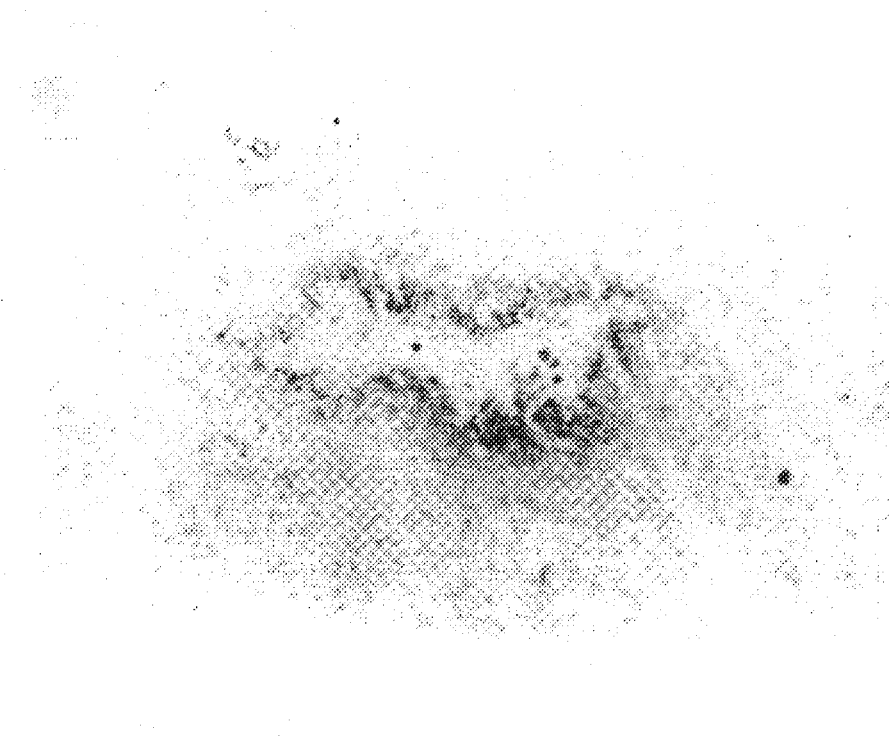
Figure 3B:
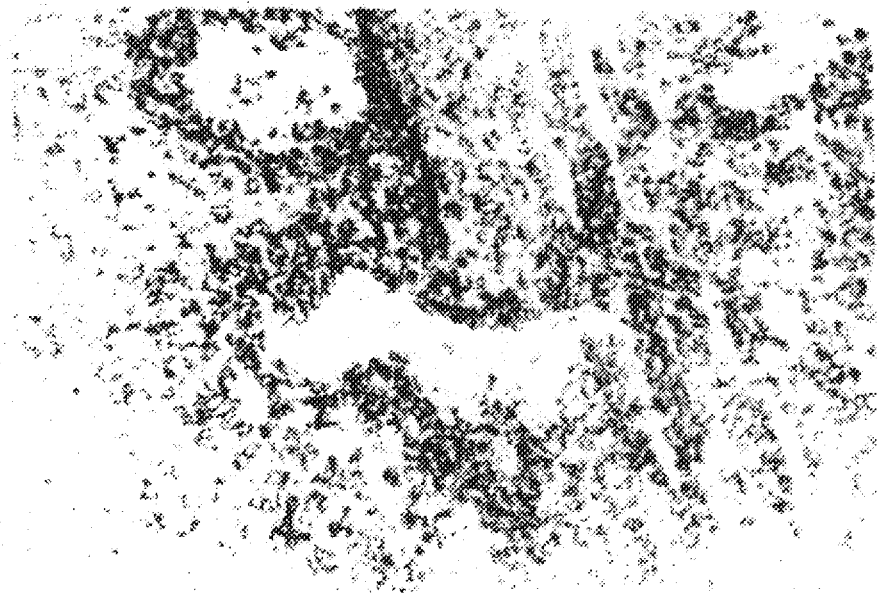
Figure 4A:
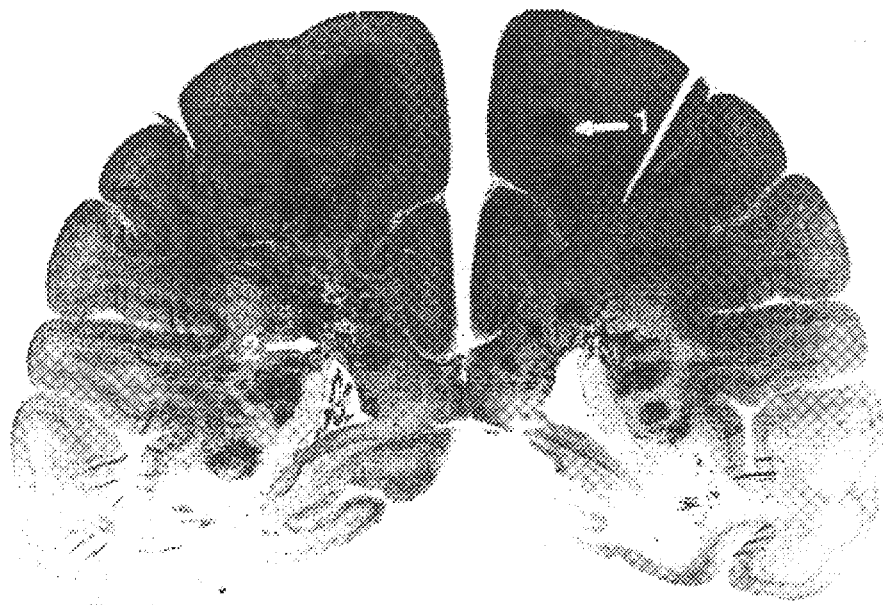
Figure 4B:
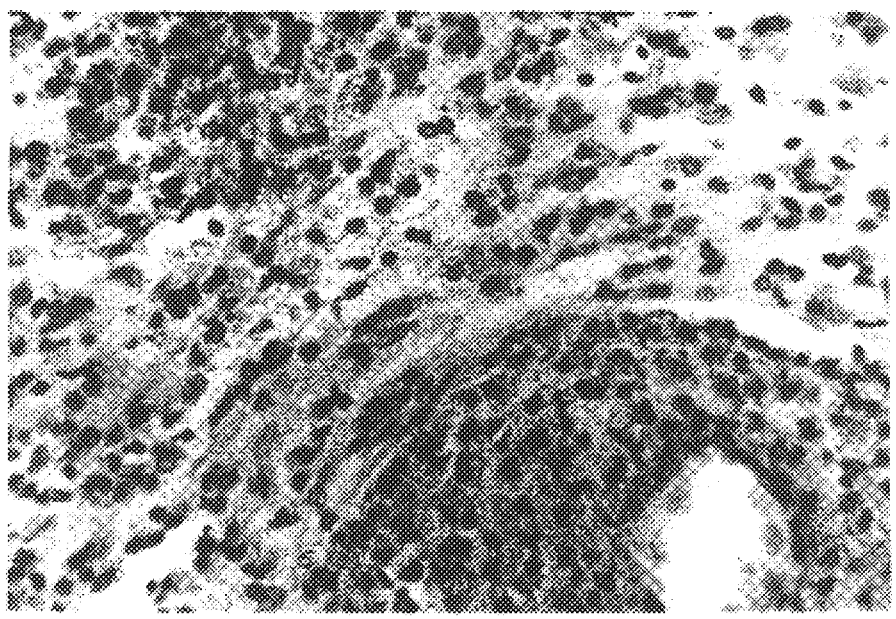
Figure 4C:
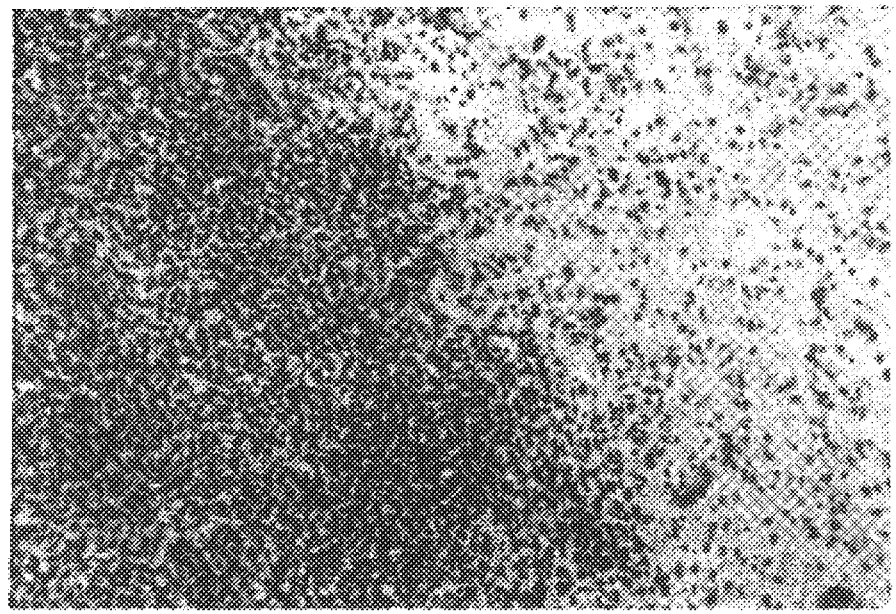
Figure 4D:
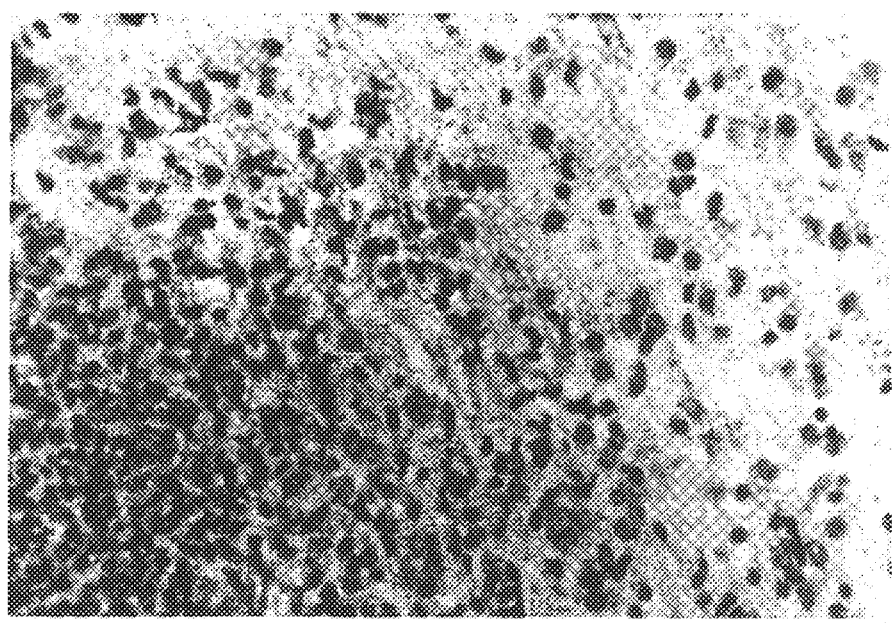
Figure 5:
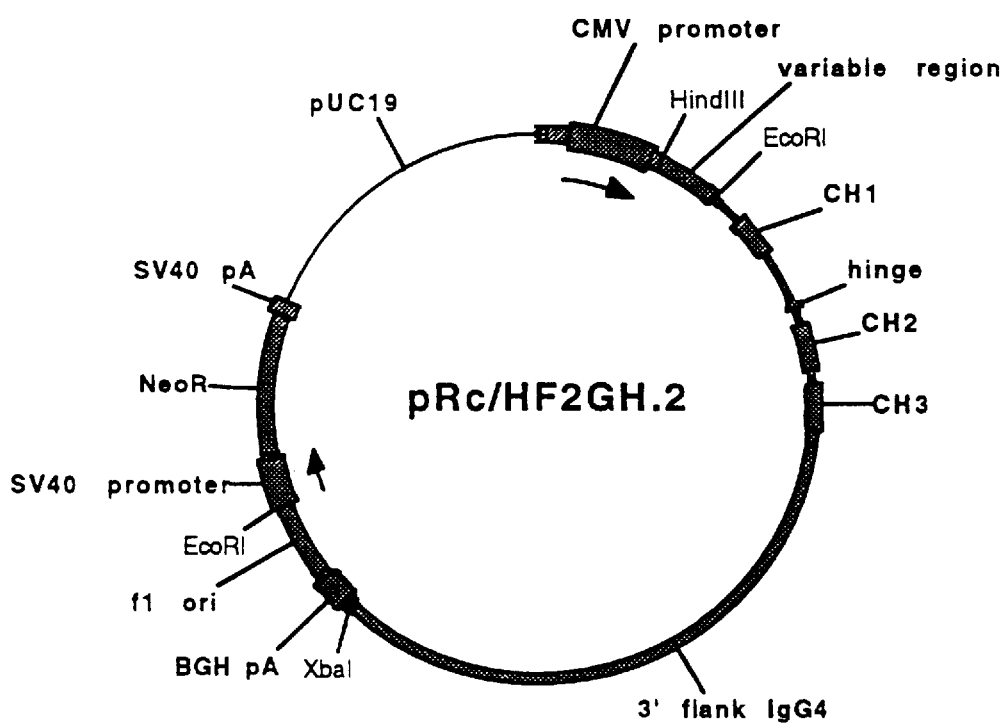
Figure 6:
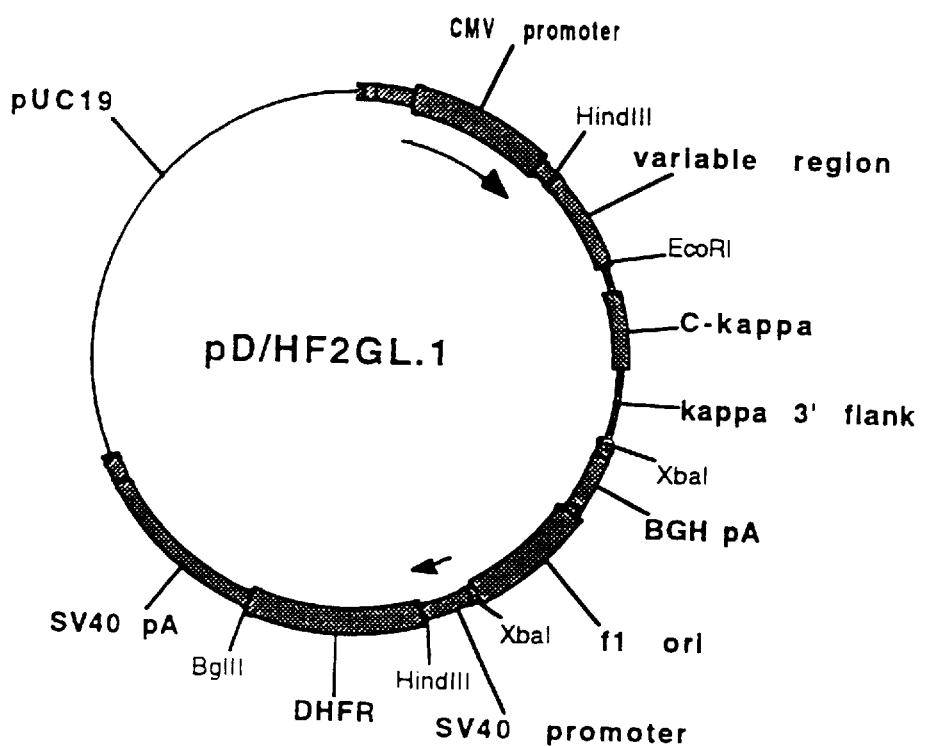

Cryostat sections of cerebellum or cerebrum were stained with hematoxylin and eosin and by the immunoperoxidase technique in conjunction with mAbs to human leukocyte membrane antigens in order to analyze the composition of the cellular infiltrates. Immunocytochemical staining with mAb 60.3, which recognizes a CD18 determinant common to all leukocytes, was used to confirm the presence of leukocytes in EAE lesions. A tissue section obtained from the brain of animal 89070 and stained with mAb 60.3 is shown in FIG. 3. In Panel A, at 390X magnification and stained with rabbit anti-mouse IgG, murine IgG coated cells are revealed in the lumen of blood vessels but not in brain tissue; and, in Panel B, at 390X magnification and stained with mAb 60.3, massive infiltration of PMBCs is seen in the exudate and extending out into adjacent white matter.

Animal 89070 was the only mAb-treated animal to die before completion of treatment. Brain tissue taken from this animal was stained with a goat anti-mouse Ig antibody in order to determine whether the treatment mAb had entered the CNS before the animal died. MAb 60.3 reacts with both leukocytes and brain microglia. If this mAb had crossed the blood-brain-barrier during the treatment period, it was expected that a staining pattern similar to that shown in FIG. 3, Panel B might be obtained. Alternatively, if the treatment mAb entered the CNS, bound only to blood leukocytes, the microglia would not have been stained. Instead, murine Ig-coated cells were only detectable in the vessel lumen, and not at all in the perivascular spaces. The absence of any positively stained leukocytes in the lesion stained with goat anti-mouse Ig, suggests that the animal died of an inflammatory condition existing before treatment was initiated and that the treatment antibody was given too late to be effective.

Effect of Treatments on Leukocyte Counts

The hematologic hallmarks of untreated EAE are a progressive leukocytosis and lymphopenia prior to the onset of clinical signs. The leukocytosis can represent as much as a four-fold increase in the number of circulating PMNC and no significant changes in the frequency or absolute numbers of monocytes, eosinophils, or basophils. Following successful treatments of EAE, the absolute numbers of lymphocytes and PMNC return, fairly soon after the initiation of treatment, to pre-sensitization levels. Thus, continuous monitoring of blood leukocytes provides a useful measure of disease progression which complements the clinical evaluation and magnetic resonance imaging.

Blood was drawn on a weekly basis until the onset of clinical disease and then more frequently. One-half ml was sent to the hematology laboratory for WBC and differential counts. The results are set out in Table 3 below providing white blood cell number ($\times 10^3$) per mm$^3$ whole blood. "NA" indicates that data was not available. A dashed line indicates that the animal was sacrificed at this time.

TABLE 3

WBC ANALYSES OF MAB-TREATED EAE ANIMALS

ANIMALS:

| Day | 89070 | 89075 | 89080 | 89069 | 89071 | 89074 |
|---|---|---|---|---|---|---|
| Presens | 8.1 | 8.7 | 14.0 | 8.0 | 7.8 | 13.3 |
| Onset | 14.6 | 16.2 | 16.3 | 9.3 | 12.3 | 18.1 |
| Day 2 | — | 27.1 | 33.2 | 22.2 | 22.6 | 49.9 |
| Day 4 | | 49.6 | 53.1 | 31.6 | 41.4 | 72.0 |
| Day 7 | | 61.2 | 61.7 | 16.4 | 90.7 | 88.6 |
| Day 10 | | 20.7 | 18.2 | 20.0 | 12.8 | 14.6 |
| Day 14 | | 33.3 | 9.6 | 8.2 | 18.4 | 13.4 |
| Day 21 | | 8.7 | 12.9 | 8.9 | 37.1 | — |
| Day 28 | | 8.7 | 19.8 | 6.7 | — | |
| Day 35 | | 7.9 | 16.4 | 6.9 | | |
| Day 42 | | NA | NA | 8.6 | | |

WBC ANALYSIS OF CONTROL EAE ANIMALS

DEXAMETHASONE CONTROL

Animal:

| | 87143 | 87125 | 87209 | 89077 | 87200 | 87069 |
|---|---|---|---|---|---|---|
| Presens | 4.7 | 6.1 | 6.7 | 13.5 | 8.9 | 14.1 |
| Onset | 9.6 | 9.0 | 14.6 | 32.2 | 12.4 | 16.3 |
| Day 2 | 3.1 | — | — | — | 5.4 | NA |
| Day 4 | 3.7 | | | | 3.6 | NA |
| Day 7 | 3.8 | | | | 7.0 | NA |
| Day 10 | 8.7 | | | | 10.7 | — |
| Day 14 | 7.9 | | | | — | |
| Day 21 | — | | | | | |

SALINE CONTROL

Animal:

| | 84228 | 84218 | 84291 | 86140 | 86187 | 86209 |
|---|---|---|---|---|---|---|
| Presens | 11.0 | 7.0 | 13.3 | 9.7 | 8.3 | 9.7 |
| Onset | 14.3 | 9.0 | 21.9 | 23.6 | 14.2 | 3.5 |
| Day 2 | 20.2 | 8.4 | 22.5 | 29.0 | — | — |
| Day 4 | 30.1 | 8.0 | — | — | | |
| Day 7 | — | — | | | | |

In animals treated with mAb 60.3 and dexamethasone, a delayed resolution of the leukocytosis was observed as compared to animals treated with dexamethasone alone as revealed in Table 3. In two of the dexamethasone-treated animals that survived 9 days or longer, the white blood cell counts dropped to pre-sensitization levels two days after the initiation of treatment. In mAb 60.3-treated animals, a pronounced leukocytosis (4–12 fold above presensitization values) was observed which lasted for the entire treatment period. In these animals, the WBC returned to presensitization levels 3–7 days only after the treatment period had ended. Transient episodes of lymphopenia and leukocytosis continued to be observed in the surviving animals, and could be correlated in some cases with episodes of clinical relapse.

Reaction of the treatment mAb with blood leukocytes was confirmed by staining cells with anti-murine Kappa chain mAb (Becton-Dickinson, San Jose, Calif.). Flow cytometric analysis was performed with a FACSCAN Analyzer (Becton Dickinson, San Jose, Calif.). Forward and right-angle scatter gates were set on lymphocytes or large polymorphonuclear granulocytes for analysis of staining patterns. The results for lymphocytes are set out in Table 4 below.

TABLE 4

% MURINE Ig-COATED CELLS

| | ANIMALS: | | | | | |
|---|---|---|---|---|---|---|
| Day | 89070 | 89075 | 89080 | 89069 | 89071 | 89074 |
| Presens | 0 | 0 | 0 | 0 | 0 | 0 |
| Onset | 0 | 0 | 0 | 0 | 0 | 0 |
| Day 2 | — | 96.6 | 97.7 | 94.2 | 96.7 | 98.2 |
| Day 4 | | 93.8 | 95.2 | 91.2 | 97.0 | 49.8 |
| Day 7 | | 95.2 | 99.1 | 94.9 | 95.4 | 27.2 |
| Day 10 | | 0 | 2.6 | 11.2 | 19.6 | 1.4 |

The dose of mAb given to the animals was in all instances sufficient to coat >95% of circulating white blood cells and, as indicated in Table 5, to maintain detectable levels of free antibody in circulation. Data in the Table represent micrograms of circulating murine IgG per $mm^3$ whole blood.

TABLE 5

CIRCULATING MURINE IgG

| | ANIMALS: | | | | | |
|---|---|---|---|---|---|---|
| Day | 89070 | 89075 | 89080 | 89069 | 89071 | 89074 |
| Presens | 0 | 0 | 0 | 0 | 0 | 0 |
| Onset | 0 | 0 | 0 | 0 | 0 | 0 |
| Day 2 | — | 65 | 70 | 15 | 28 | 34 |
| Day 4 | | 80 | 70 | 65 | 25 | 15 |
| Day 7 | | 90 | 58 | 4 | 7 | 28 |
| Day 10 | | 0 | 0 | 0 | 0 | 0 |

After 7 days, the injected mAb was no longer detectable in the circulation. The disappearance of the murine Ig coincided with the appearance of monkey anti-murine Ig antibodies in the circulation of each animal.

Neuropathology

To confirm the diagnosis of EAE, the brains and spinal cords of each BP-sensitized animal were examined postmortem. The animals were euthanized by Nembutal overdose and brains and spinal cords were removed and dissected so that fresh-frozen samples could be obtained before the larger blocks were fixed in 10% neutral formalin. Representative blocks of tissue were embedded in paraffin and sections were stained with hematoxylin and eosin, gallocyanin-Darrow red, luxol fast blue (LFB) combined with periodic acid Schiff (PAS) and hematoxylin and with Holmes' axon stain alone or combined with LFB to differentiate demyelination from necrosis. Frozen sections of mirror-image blocks were stained with Oil Red O (ORO) [Kil, Stain Technology, 47:271, (1972)] to identify lipid-filled macrophages.

All eighteen EAE animals were evaluated histologically postmortem for evidence of EAE. All had microscopic evidence of either mild to severe acute EAE or hyperacute EAE that generally correlated with the severity and duration of the disease. All but 2 of the 12 control animals showed either predominantly hyperacute lesions characterized by hemorrhages, subtotal necrosis, demyelination, and diffuse massive infiltrations of neutrophils into the CNS parenchyma; or severe acute perivascular lesions which were more compact, more confined to the perivascular spaces than the hyperacute lesions and composed predominantly of lymphocytes and macrophages, but some neutrophils, and with abundant demyelination as well as some axonal debris. The two exceptional control monkeys, with EAE of 13–17 days duration, had a mixture of lesions ranging from mild to severe demyelinating lesions, composed predominantly of lymphocytes and macrophages with abundant myelin debris and little or no axonal reaction. All but one of the mAb-treated monkeys had a combination of: (a) older well developed demyelinated plaques with abundant myelin debris, sudanophilic lipid and little or no axonal reaction or lymphocytic infiltrate; and (b) more recent lesions corresponding to the terminal untreated relapses, which were compact, confined to perivascular spaces, with varying proportions of lymphocytes, monocytes, or neutrophils (consistent with diagnoses of mild to severe acute EAE ) and some myelin debris. These two types of lesions, found in the same animal (#89069), are shown in FIG. 4.

In FIG. 4, Panel A, at two-fold magnification, numerous inflammatory (area 1) and/or demyelinating (area 2) lesions can be ascertained in the white matter; in Panel B, at 325X magnification, area 2 of Panel A is revealed as being composed predominantly of macrophages scattered diffusely through the tissue and about blood vessels, with the small black granules constituting PAS positive glycolipoproteins; and in Panels C and D, at 130X and 325X magnification, respectively, area I of Panel A is revealed as being composed predominantly of PMNCs and no PAS positive insoluble glycoproteins.

Summary Of Results

Monitoring disease progression by a combination of clinical evaluation, blood cell fluctuations, and magnetic resonance imaging (MRI) revealed the following. Antibody treated animals survived significantly longer than either dexamethasone- or saline-treated animals ($p<0.02$; $p<0.001$; respectively). The effectiveness of this therapy is further confirmed by visualization by magnetic resonance imaging (MRI). The almost complete disappearance of major lesions in the brainstems of three different animals was unprecedented as brainstem lesions are rapidly fatal in untreated animals. The disappearance of MRI-detectable lesions following administration of mAb 60.3 demonstrates a potent effect on the inflammatory reactions producing edema in the brain lesions. MAb 60.3 is known to inhibit plasma leakage in vivo [Arfors et al., Blood, 60:338–340, (1987)], probably the most important factor in improvement in MRI-detectable lesions, as changes in the tissue water characteristics can be visualized by changes in image intensity on the MRI scans.

The severity of clinical signs at the onset of EAE was not uniform because individual monkeys responded differently to sensitization with myelin BP. Nevertheless, there was no correlation between the severity of clinical signs at the onset of EAE and the ability of animals to respond to treatment. Of the six mAB-treated animals, four were + at the onset of clinical signs and 2 were ±. Of the twelve control animals (six dexamethasone-treated and six saline-treated), 8 were + and 4 were ±, essentially the same distribution as the mAb-treated group. No correlation was found between the severity of clinical signs at the onset and the potentially stressful procedure of MRI examination under general anesthesia. Of the ten animals scanned by MRI, six were + at the onset of clinical disease and four were ±. One might have expected the additional handling involved in scanning the animals, as well as the frequent administration of anesthetics, to result in a generalized suppression of the immune response. [Wall et al., Lab Animals, 19:138–144 (1985), Thomas et al., Clin. Exp. Immunol., 47:457–466 (1982)]. However, the results do not support this hypothesis.

The dexamethasone-treated animals did have longer mean survival time (7 days) than the saline-treated controls (3 days), but the difference was not statistically significant ($p<0.1$). Thus, although dexamethasone slowed down the disease process, it had little apparent effect on the final outcome of the disease. Co-administration of mAb 60.3, on the other hand, significantly prolonged survival and in some cases completely reversed the clinical and MRI appearances of EAE.

EXAMPLE 4

Six to twelve week old Balb/c mice (Charles River Biotechnical Services, Inc., Wilmington, Mass., IACUC #901103) were immunized with human T cell line Hut 78 to generate anti-CD18 antibodies. For each of two hybridoma-generating fusions (designated fusions 22 and 23) two Balb/c mice were bled retro-orbitally for the collection of pre-immune serum on day 0. On day 2, each animal received a total of $5 \times 10^6$ Hut 78 cells in 0.2 ml sterile PBS intravenously. The mice were then immunized at two week intervals for six weeks and then at monthly intervals for three months. The final monthly boost was of glutaraldehyde fixed Hut 78 cells. Cells were fixed by mixing equal volumes of cells ($2 \times 10^7$) and glutaraldehyde (0.1% so that the final concentration of the fixative was equal to 0.05%. The mixture was incubated with swirling for thirty seconds and an equal volume of 0.2M glycine (in PBS) was added to block the reaction. The reaction mixture was washed once with 0.2M glycine (in PBS) and twice with PBS. Cells were resuspended in PBS at a concentration of $5 \times 10^6$ cells per 0.2 ml PBS. Immune serum was collected via retro-orbital bleeding on day 56 and tested by FACS to determine its reactivity with the immunogen (Hut 78 cells). Three days prior to the projected fusion date, the animals were immunized by intravenous injection with a final dose of $5 \times 10^6$ glutaraldehyde fixed cells.

For each fusion, the spleen from the mouse displaying the highest immune serum titer against the immunogen was removed sterilely. A single-cell suspension was formed by grinding the spleen between the frosted ends of two glass microscope slides submerged in serum free RPMI 1640, supplemented with 2 mM L-glutamine, 1 mM sodium pyruvate, 100 units/ml penicillin, and 100 $\mu$g/ml streptomycin (RPMI)(Gibco, Canada). The cell suspension was filtered through sterile 70-mesh Nitex cell strainer (Becton Dickinson, Parsippany, N. J.), and washed twice by centrifuging at 200 g for 5 minutes and resuspending the pellet in 20 ml serum free RPMI. Thymocytes taken from 3 naive Balb/c mice were prepared in a similar manner.

NS-1 myeloma cells, kept in log phase in RPMI with 11% fetal bovine serum (FBS)(Hyclone Laboratories, Inc., Logan, Utah) for three days prior to fusion, were centrifuged at 200 g for 5 minutes, and the pellet was washed twice as described in the foregoing paragraph. After washing, each cell suspension brought to a final volume of 10 ml in serum free RPMI, and 10 $\mu$l was diluted 1:100. 20 $\mu$l of each dilution was removed, mixed with 20 $\mu$l 0.4% trypan blue stain in 0.85% saline (Gibco), loaded onto a hemacytometer (Baxter Healthcare Corp., Deerfield, Ill.) and counted.

For each fusion, $2 \times 10^8$ spleen cells were combined with $4 \times 10^7$ NS-1 cells, centrifuged and the supernatant was aspirated. the cell pellet was dislodged by tapping the tube and 2 ml of 37° C. PEG 1500 (50% in 75 mM Hepes, pH 8.0)(Boehringer Mannheim) was added with stirring over the course of 1 minute, followed by adding 14 ml of serum free RPMI over 7 minutes. An additional 16 ml RPMI was added and the cells were centrifuged at 200 g for 10 minutes. After discarding the supernatant, the pellet was resuspended in 200 ml RPMI containing 15% FBS, 100 $\mu$M sodium hypoxanthine, 0.4 $\mu$M aminopterin, 16 $\mu$M thymidine (HAT) (Gibco), 25 units/ml IL-6 (Boehringer Mannheim) and 1.5× $10^6$ thymocytes/ml. The suspension was dispensed into ten 96-well flat bottom tissue culture plates (Corning, United Kingdom) at 200 $\mu$l/well. Cells in plates were fed on days 2, 4 and 6 days post fusion by aspirating approximately 100 $\mu$l/well plating medium described above except containing 10 units/ml IL-6 and lacking thymocytes.

On day 10 culture supernatants were taken from each well, pooled by column or row and analyzed for the presence of an antibody capable of competing with an FITC-60.3 conjugate (prepared according to Goding, in "Monoclonal Antibodies: Principles and Practice," 2d Ed., p. 241–280, Academic Press, N.Y., 1986) for binding to Hut78 cells. The competition assay was performed as follows. Twenty-five $\mu$l of a cell suspension containing $10 \times 10^6$ Hut78 cells/ml was combined with 25 $\mu$l of a sub-saturating dose of FITC-60.3 ($\times 2560 \cong 0.8$ $\mu$g/ml) and 50 ml $\mu$l of fusion supernatant and incubated for 30 min at 4° C., washed by adding culture media to the cell mixture and centrifuging at 1800 rpm for three minutes. The supernatant was removed by aspiration and the pellet was washed twice with flow cytometric analysis (FACS) medium containing RPMI, 2% PBS and 0.1% NaN$_3$. The reaction mixture was fixed by addition of 1% paraformaldehyde (pH 7.2 in PBS) and transferred to polystyrene tubes for FACS using a Becton Dickenson FACscan analyzer. Of the 960 hybridomas generated in fusion 22, the supernatant of hybridoma No. 22F12C inhibited binding of FITC-60.3 by about 90%; supernatants from hybridoma Nos. 22J4A and 22B3B inhibited binding by about 40% and 10% respectively. Two hybridomas from fusion 23, 23F2G and 23I11B, produced antibodies which inhibited FITC-60.3 binding by $\geq 95\%$. These five hybridomas were cloned. Hybridoma cell line 23F2G was deposited with the American Type Culture Collection, 12301 Parklawn Drive, Rockville, Md. 20852 U.S.A. on Jun. 30, 1992 and accorded accession number A.T.C.C. HB 11081. The isotype of the antibody produced by hybridoma cell line 23F2G (referred to herein as mAb 23F2G) was determined to be IgG2a. Hybridomas 22F12C and 23I11B also produced antibodies of the IgG2a isotype, while hybridomas 22B3B and 22J4A produced IgGI antibodies.

Antibodies from hybridomas 22F12C, 23F2G and 23I11B were all found, in varying degrees, to: (1) block adhesion of human T cells to activated HUVEC monolayers; (2) block aggregation of 13-acetate (PMA) activated Con A blast cells phorbol 12-myristate; and (3) induce demargination of white blood cells in rabbits. The ability of the IgGl antibodies produced by hybridomas 22B3B and 22J4A to block adhesion is as yet undetermined; mAb 22J4A was able to block aggregation, but mAb 22B3B was not; both antibodies induced demargination, but to a lesser degree than the others or mAb 60.3. Based on the screening results noted above, it appears likely that, notwithstanding the ability to compete for binding of mAb 60.3 to LFA-1 on Hut 78 cells, mAb 22B3B and 22J4A are specific for an epitope present on the CD11a component of LFA-1 or an epitope associated with the CD11a/CD18 heterodimer rather than with an epitope of CD18.

A comparison was made between the amino acid sequence of the variable region of mAb 60.3 presented by L. Harris at San Francisco, Calif. on May 26–27, 1992 in a poster presented at a conference entitled "Cell Adhesion Molecules In Inflammation" organized by International Business Communications (South Natick, Mass.) and the amino acid sequence of the variable region of mAb 23F2G. Gross differences were found, despite the fact that 23F2G competed with 60.3 for binding to Hut78 cells. While these differences are suggestive of the possibility that the antibodies bind adjacent, different epitopes on CD18, confirmation of this possibility will have to await definitive epitope mapping studies.

EXAMPLE 5

Hybridoma 23F2G was amplified by the ascites method and antibody was purified by affinity chromatography on Protein A under pyrogen-free conditions. From 25 ml of ascites, 120 mg of antibody preparation was isolated. This preparation contained only about 4 endotoxin units per mg.

Two *Macaca fascicularis* monkeys were then involved in a study to preliminarily determine the ability of mAb 23F2G to alleviate EAE symptoms. The EAE induction procedures were essentially as in Example 1. Two animals, Nos. 89161 and 89186, sensitized to 1.0 mg of purified monkey basic protein and developed hyperacute hemorrhagic EAE 18 and 20 days post sensitization, respectively. Animal 89161 died within 12 hours of onset and before treatment with dexamethasone could be initiated. Animal 89186 was treated for a week with both dexamethasone (3 days at 4 mg/kg, 2 days at 2 mg/kg and 2 days at 1 mg/kg) and mAb 23F2G (7 days at 2 mg/kg, i.v.). The animal improved dramatically with complete resolution of paralysis three days after initiation of treatment. Lesions detected by MRI resolved four days after cessation of treatment and the animal improved dramatically with complete resolution of paralysis. Eight days following cessation of treatment, the animal relapsed and was sacrificed. Hematologic analysis revealed that mAb 23F2G caused steady demargination of leukocytes which peaked on the last day of treatment. The white blood cell count rose from $22.7 \times 10^3$ on the day of clinical onset to $82 \times 10^3/mm^3$ on the last day of treatment. The antibody showed saturation of blood lymphocytes at the dose administered.

EXAMPLE 6

Humanization of 23F2G Antibody Variable Regions
A. Determination of Variable Region Sequences Total RNA was isolated from the hybridoma cell line 23F2G (A.T.C.C. HB 11081) and first strand cDNA was synthesized using the total RNA as a template. The first strand cDNA was in turn used as a template for PCR reactions to obtain double-stranded DNA fragments encoding the variable regions of both the heavy and light chains of mAb 23F2G.

The forward primer used to clone the heavy chain variable region was primer HFR1–4, the sequence of which is set out below in IUPAC nomenclature as SEQ ID NO: 1.

Forward Primer HFR1–4 (SEQ ID NO: 1)
CGATAC<u>GAATTC</u>AGGTSMARCTGCAGSAGTCWG

The 3' nucleotides of the primer correspond to the region encoding the first seven amino acids of mature mouse immunoglobulin heavy chains, while the underlined nucleotides of the primer encode an EcoRI site to facilitate cloning of the PCR fragment generated. The reverse primer used to clone the heavy variable region sequences was primer HG2A-1, the sequence of which is set out below in IUPAC nomenclature as SEQ ID NO: 2.

Reverse Primer HG2A-1 (SEQ ID NO: 2)
GCTATC<u>GGATCC</u>GGARCCAGTTGTAYCTCCACA CAC The 3' end of primer HG2A-1 encodes the complement of codons 127–136 in the mouse $IgG_{2A}$ constant region [according to the numbering system of Kabat et al., "Sequences of Proteins of Immunological Interest", U.S. Department of Health and Human Services, NIH Publication No. 91–3242 (1991)] and the underlined nucleotides of the primer encode a BamHI site.

The forward primer used to generate PCR fragments encoding the light chain variable region was primer LFR1–3, the sequence of which is set out below in IUPAC nomenclature as SEQ ID NO: 3.

Forward Primer LFR1–3 (SEQ ID NO: 3)
CGATAC<u>GAATTC</u>GATRTTKTGATGACYCARRCT SCA The 3' end of primer LFR1–3 corresponds to the mature amino-terminal region of the mouse immunoglobulin light chain (residues 1–8) and the underlined nucleotides encode an EcoRI site to facilitate cloning. The reverse primer for the light chain variable region was primer LKC-1, the sequence of which is set out below as SEQ ID NO: 4.

Reverse Primer LKC-1 (SEQ ID NO: 4)
GCTATC<u>GGATCC</u>ACTGGATGGTGGGAAGATGGA

The 3' end of primer LKC-1 is complementary to codons 116–122 in the constant region of the mouse kappa light chain gene (according to the numbering system of Kabat et al., supra). The underlined nucleotides in the primer encode a BamHI site.

The resulting light and heavy chain PCR fragments were ligated into different vectors and eight to twelve independent clones were sequenced on both strands. The DNA and amino acid sequences corresponding to the heavy chain variable region of 23F2G are shown in SEQ ID NO: 5. The seven amino-terminal residues of the heavy chain sequence are indefinite because they correspond to the forward primer used in the PCR reaction. Amino acid residues 1 to 15, 31 to 45, 53 to 84 and 94 to 103 of SEQ ID NO: 5 comprise the framework regions of the mouse 23F2G heavy chain variable domain while amino acid residues 16 to 30, 46 to 52 and 35 to 93 of SEQ ID NO: 5 comprise the CDR regions. Comparison of the translated heavy chains variable sequence to the different subgroups of variable regions of mouse heavy chains [Kabat et al., supra] indicates that the heavy chain variable sequence of 23F2G belongs in mouse subgroup II. The DNA and deduced amino acid sequences of the light chains variable region of 23F2G are shown in SEQ ID NO:6. The eight amino-terminal residues of the light chain were elucidated through amino-terminal sequencing of the light chain protein. Amino acid residues 1 to 30, 36 to 49, 67 to 98 and 110 to 120 of SEQ ID NO: 6 comprise the framework regions of the mouse 23F2G light chain variable domain while amino acid residues 31 to 35, 50 to 66 and 99 to 109 of SEQ ID NO: 5 comprise the CDR regions. The light chain variable region of 23F2G is most similar to the subgroup III mouse light chain variable regions [Kabat et al., supra].

B. Design of Humanized Heavy and Light Chain Variable Regions

In choosing human frameworks, two general criteria were used: (1) the human frameworks chosen were as homologous as possible to those of 23F2G in order to increase the probability that the CDR regions would retain their correct conformations and consequently their affinity towards the antigen [see Kabat, et al., supra, and Kirkham et al., *EMBO J.*, 11:603–609 (1992)] and (2) the human framework regions chosen contained a minimal number of unusual residues that could potentially provoke an immune response against the antibody in a human.

Because the heavy chain of mAb 23F2G resides in the mouse subgroup II sequences, it is most homologous to sequences in human subgroup I. Therefore, a framework from the human subgroup I set of heavy chain variable sequences was chosen for use in a humanized version of mAb 23F2G. Rather than choose a particular framework from existing sequenced human antibodies, it was decided to use a consensus sequence for the human subgroup I variable region framework (Kabat, et al., supra) so that the unusual residues often found in particular frameworks were avoided. The combined framework regions of the heavy chain of 23F2G, excluding the amino-terminal seven amino acids, have 70% sequence identity to the human subgroup I consensus sequence. In comparison, the combined 23F2G heavy chain framework regions were less homologous to the human subgroup II and III consensus sequence (52% and 58%, respectively).

Replacement of rodent antibody framework regions with human framework sequences can result in an antibody with significantly reduced binding affinity. In such cases, it is necessary to substitute certain human framework residues with those in the original rodent antibody. Based on an analysis of published antibody humanization studies including Co et al., *J. Immunol.*, 148:1149–1154 (1992); Carter et al., *Proc. Nat'l. Acad. Sci.(U.S.A.)*, 89:4285–4289 (1992); Maeda et al., *Hum. Antibod. Hybridomas*, 2:124–134 (1991); Kettleborough et al., *Protein Engineering*, 4(7):773–783 (1991); Tempest et al., BIO/TECHNOLOGY, 9:266–271 (1991); Gorman et al., *Proc. Nat'l. Acad. Sci. (U.S.A.)*, 88:4181–4185 (1991); Queen et al., *Proc. Nat'l. Acad. Sci.(U.S.A.)*, 86:10029–10033 (1989); and Co et al., *Proc. Nat'l. Acad. Sci.(U.S.A.)*, 88:2869–2873 (1991), it was decided to retain the framework residues of mouse 23F2G at positions 66, 67 and 93 (numbering system of Kabat et al., supra) which correspond to amino acid positions 60, 61 and 90 of SEQ ID NO: 5, rather than use the human subgroup I residues at these positions in the humanized heavy chain.

A similar rationale was followed in humanizing the 23F2G light chain variable domain. The variable region framework sequences of the light chain of 23F2G are 71%, 69% and 72% identical to the human subgroup I, II, and III kappa consensus sequences, respectively. It was decided to use the human kappa subgroup I consensus framework sequence because it was highly homologous to that of 23F2G and because subgroup I frameworks have most commonly been used to humanize light chain variable regions. No mouse-specific residues were substituted in the light chain human framework regions.

The sequences designed for the humanized form of the 23F2G light and heavy variable regions consisted of the framework regions of the human variable region framework sequences as described above and the CDR regions of mouse mAb 23F2G. The DNA and deduced amino acid sequences of these humanized heavy and light chains variable regions are presented in SEQ ID NOs: 7 and 8, respectively. Amino acids residues 1 to 30, 36 to 49, 67 to 98 and 110 to 120 of SEQ ID NO: 7 comprise the framework regions of the humanized heavy chain variable domain, while amino acids residues 31 to 35, 50 to 66 and 99 to 109 of SEQ ID NO: 7 comprise the CDR regions. Amino acids residues 1 to 23, 39 to 53, 61 to 92 and 101 to 111 of SEQ ID NO: 8 comprise the framework regions of the humanized light chain variable domain, while amino acids residues 24 to 38, 54 to 60 and 93 to 100 of SEQ ID NO: 8 comprise the CDR regions.

C. Assembly of Humanized 23F2G Variable Region Domains

Two DNA fragments which together encoded the humanized version of the heavy chain variable region of 23F2G were assembled from complementary synthetic oligonucleotides 50–60 nucleotides in length. Sequences included in addition to sequences encoding the variable domain were (1) a HindIII restriction site at the 5' end to facilitate attachment to a promoter sequence, (2) an optimal translation initiation sequence just upstream of the initiator methionine, (3) DNA encoding a signal peptide, (4) a splice donor site just 3' to the variable region, and (5) an EcoRI site at the 3' end to facilitate attachment to the constant region DNA segment. The DNA sequence encoding the signal peptide was designed to be the same as that encoding the signal peptide associated with several human heavy chain subgroup I sequences (Kabat et al., supra). Two DNA fragments together encoding the humanized light chain variable region DNA segment were also constructed from complementary synthetic oligonucleotides. The assembled heavy and light chain variable region DNA fragments were then cloned into pSK+ (Stratagene, La Jolla, Calif.) and their sequence was confirmed.

D. Construction of a Humanized 23F2G Heavy Chain Expression Vector

A plasmid for expression of the humanized heavy chain of 23F2G was constructed by ligating together the two DNA fragments containing the humanized heavy chain variable region sequence, the constant regions of the human $IgG_4$ gene [cloned from a human T cell line (Hut 78)], and the expression vector pRc/CMV (Invitrogen). The expression vector pRc/CMV contains the immediate early promoter from the cytomegalovirus (CMV), a polylinker region downstream of the promoter, and a neomycin resistance cassette. Specifically, the following four fragments were isolated and ligated: (1) the 5.5 kb HindIII/XbaI fragment from pRc/CMV, (2) a 6 kb EcoRI/XbaI fragment containing the $IgG_4$ sequences, (3) a ~200 bp HindIII/XhoI fragment containing the 5' half of the humanized heavy chain variable region sequence, and (4) a ~300 bp XhoI/EcoRI fragment containing the 3' half of the heavy chain variable region sequence.

The ligation mix was used to transform *E. coli*, and a correct clone was confirmed by restriction digest and was designated pRc/HF2GH.2. A circular map of pRc/HF2GH.2 is shown in FIG. 1. Large scale plasmid preparations of pRc/HF2GH.2 were performed using the alkaline lysis method as described in Sambrook et al., *Molecular Cloning: A Laboratory Manual*, Cold Spring Harbor Press (1989) and the plasmid was twice-banded in CsCl-ethidium bromide gradients.

E. Construction of a Humanized 23F2G Light Chain Expression Vector

A plasmid for expression of the humanized light chain was constructed by ligating together two DNA fragments containing the humanized light chain variable region sequence, the human kappa gene, a dihydrofolate reductase (DHFR) gene expression cassette, and a part of the pRc/CMV vector containing the strong promoter from CMV.

In constructing a plasmid containing the humanized light chain gene of 23F2G and DHFR sequences, several intermediate plasmids were first constructed. The first intermediate plasmid constructed, pRc/HF2GL.1, was similar to that made for expression of the heavy chain gene in that the variable and constant region coding sequences were cloned between the HindIII and XbaI sites of pRc/CMV. To create pRc/HF2GL.1 the following 5 fragments were ligated together: (1) HindIII/XbaI digested pRc/CMV, (2) a ~200 bp HindIII/Asp718 fragment containing the 5' half of the humanized light chain variable region sequence, (3) a ~200 bp Asp718/EcoRI fragment containing the 3' half of variable region gene, (4) a ~400 bp EcoRI/SacI fragment containing the 5' half of kappa gene fragment (cloned from a human genomic DNA library) and (5) a ~350 bp SacI/XbaI fragment containing the 3' half of kappa gene fragment (also cloned from the human genomic DNA library).

A second intermediate plasmid, pSl1190-dhfr, was made by inserting a 1.7kb SphI/BamHI fragment from pSV2-dhfr (ATCC 37146) into the corresponding site in the polylinker of the sequencing vector pSL1190 (Pharmacia, Piscataway, N.J.). The SV40-DHFR sequences within pSL1190-dhfr were completely sequenced and were found to contain only minor differences from previously published sequence of these elements. In particular, the DHFR coding sequence within pSL1190-dhfr was found to encode the same polypeptide as the previously published sequence of mouse DHFR [Simonsen and Levinson, *Proc. Natl. Acad. Sci. U.S.A.*, 80:2495–2499 (1983)].

To create a final plasmid (pD/HF2GL.1) for expression of humanized 23F2G light chain, the following four fragments were ligated: (1) the 3.1 kb BamHI/HindIII fragment from pRc/CMV, (2) the 0.753 bp XbaI/Asp718 fragment from pRc/CMV, (3) the 1.2 kb fragment from pRc/HF2GL. 1 (containing the complete humanized light chain gene), and (4) the 1.7 kb Asp718/BamHI fragment (containing SV40 promoter-DHFR sequences) from pSL1190-dhfr. A circular map of pD/HF2GL.1 is shown in FIG. 2. Large scale preparations and purifications of these plasmids were performed as described above for the heavy chain expression plasmid.

F. Transfection of the CHO Cell Line DXB11 and Gene Amplification

Lipofection was used to introduce both the heavy and light chain expression plasmids into the dhfr⁻ CHO cell line DXB11. Similar dhfr⁻ CHO cell lines are described in Urlaub, et al, *Proc. Natl. Acad. Sci. U.S.A.*, 77.–4216–4220 (1980). Selection for cells that were able to grow in the absence of nucleosides (selects for DHFR) and that were resistant to G418 (neomycin) ensured that transfectants contained both plasmids.

A pool of three transfectants was subjected first to 25 nM and then 100 nM methotrexate (Sigma, St. Louis, Mo.) to select cells that had undergone amplification of the DHFR gene. After limited dilution cloning, one resulting cell line, designated 6E6 (A.T.C.C. CRL 11398) was found to produce humanized 23F2G at a rate of about 1 ng/cell/day and accumulate 5–10 mg antibody per liter of growth medium. Another cell line derived by transfection of the dhfr⁻ CHO cell line [Urlaub, et al., *Cell*, 33:405–412 (1983)] was isolated in a similar manner to cell line 6E6 and was named B13–24 (A.T.C.C. CRL 11397). Cell line B13–24, which is resistant to 200 nM methotrexate, produces over 100 mg/l of antibody at a rate of about 25 pg/cell/day.

The 6E6 and B13–24 cell lines can be cultured in Dulbecco's modified Earls Medium/Ham's F-12 (1:1 mix) with 5% heat inactivated fetal bovine serum at 37° C., 6% carbon dioxide and 100% humidity, and at a density of between 2×10⁵ and 6×10⁵ cells per milliliter. The media for the 6E6 cell line includes 100 nM methotrexate while the media for B13–24 cell line includes 200 nM methotrexate.

Humanized 23F2G antibody was purified from the 6E6 and B13–24 cell lines as follows. Cell harvest fluid was first passed through a Protein A column, which binds IgGs. The column was washed with 35 mM Tris buffer, 0.1% Tween 20, pH 7.85 and then with 50 mM citrate, pH 5.0. The antibody was eluted with 50 mM citrate, 0.02% Tween 20, pH 3.0, and kept under acidic conditions at room temperature for 15 minutes. The eluate was then chilled to 2°–8° C. and neutralized with cold 1M Tris buffer. The Protein A eluate was adjusted to 0.5M ammonium sulfate, 25 mM Tris, pH 8.0 and loaded onto a Phenyl Sepharose column. The column was then washed with loading buffer (0.5M ammonium sulfate, 25 mM Tris, pH 8.0), and eluted with 0.1M ammonium sulfate, 25 mM Tris, pH 8.0. The eluate was then diluted ¹⁄₁₀ with purified water to prepare it for the next step. The diluted phenyl sepharose eluant was loaded onto a DEAE Sepharose Fast Flow column that has been equilibrated with 10 mM Tris, pH 7.5. After loading, the column was washed with 10 mM Tris, pH 7.5, followed by 10 mM Tris, 50 mM NaCl, pH 7.5. The antibody was eluted with 10 mM Tris, 200 mM NaCl, pH 7.5. The DEAE eluate is loaded onto a Sephadex G-25 Superfine column, and washed through with the final formulation buffer (50 mM sodium acetate, 120 mM NaCl, 0.02% Tween 20, pH 5.6). The eluted antibody was then diluted to the required concentration.

G. The Heavy Chains Derived from Cell Lines 6E6 and B13–24

During the course of analysis of mRNA derived from cell line 6E6 it was noted that most (but not all) of the RNA encoding the humanized 23F2G heavy chain was longer than expected. Subsequent cloning and sequencing of several cDNAs encoding the heavy chain revealed that a region in the DNA near that encoding the C-terminus had undergone a recombination event such that the sequence encoding the Gly-Lys sequence typically found at the C-termini of IgG₄ heavy chains was missing and was replaced by the sequence encoding Asp-Ser-Asn-Leu-Trp-Asn (SEQ ID NO: 9).

The heavy chain mRNA derived from the cell line B13–24 is the expected size and therefore the C-terminal coding region of the heavy chain produced by cell line B13–24 is likely to be intact.

H. Affinity of the Humanized 23F2G Antibodies

Humanized 23F2G antibody competes effectively with flourescent murine 23F2G antibody in a cell binding assay. Fluorescent murine 23F2G antibody at 0.4 μg/ml was mixed with increasing amount of humanized 23F2G antibody. These antibody mixtures were incubated with the LFA-1 positive cell line HUT-78. After washing the cells were examined by flow cytometry for mean fluorescent intensity. In this assay humanized 23F2G antibody (at 1.01 μg/ml) bound to LFA-1 positive cells as efficiently as murine 23F2G antibody.

EXAMPLE 7

In order to further characterize the effects of murine monoclonal antibody 23F2G (referred to in this example as "M23F2G") and the humanized antibody obtained from CHO 6E6 cells of Example 6 ("Hu23F2G"), additional *Macaca Fascicularis* monkeys were sensitized to myelin BP in the manner of Example 1 using 0.1 ml of a freshly prepared, somewhat more potent emulsion comprising 0.1–0.4 mg of monkey BP and 0.5 mg of heat-killed *M. tuberculosis*. M23F2G was purified from ascites fluid as in Example 5 and contained 5.2 endotoxin units per mg. Hu23F2G was purified from CHO cell 6E6 (A.T.C.C. CRL 11398) culture supernatant by affinity chromatography on Protein A under pyrogen-free conditions and contained 1.2 endotoxin units per mg.

Treatment was started on the day of onset of disease. Treatment groups consisted of dexamethasone (4 mg/kg/day for 3 days) alone, dexamethasone plus M23F2G (2 mg/kg/day for 7 days), or dexamethasone plus Hu23F2G (2 mg/kg/day for 7 days). Treatment assignment of animals was made prior to the onset of clinical disease. Seven animals were treated with dexamethasone, five with M23F2G, and four with Hu23F2G.

The endpoints used to evaluate the effects of treatment were: overall survival after onset of disease up to a maximum of 42 days; clinical score following treatment; and lesion burden (determined by MRI) following treatment. Clinical signs were monitored daily until time of death or sacrifice. Animals were scanned by MRI once a week. A modified clinical scoring system (vis-a-vis the previous scoring system in Table 1) was used to reflect the severity of disease and is set out in Table 6, below. Pre-treatment MRI scan data was obtained at onset (±3 days) of clinical disease; post-treatment scan data was obtained on 10 days after clinical onset (±3 days). MRI scans were analyzed by the software package NIH Image Version 1.44 (Bethesda, Md.) to quantitate areas of abnormality. These MRI lesions reflect brain edema and cellular infiltration caused by EAE and allow a non-invasive method of assessing the effect of treatment on brain inflammation.

TABLE 6

CLINICAL SIGNS AND GRADES OF EAE IN MACAQUES

Score  Clinical Sign

1  Anorexia, weight loss
2  Inactivity, slow response, facial rash, hyperactivity, yawning
3  Apathy, drooling
4  Nystagmus, transient tremor
5  Hypokinesis, clumsiness
6  Ataxia, pupillary signs, ptosis strabismus, blindness
7  Head tilt, tremor
8  Seizure, body twisting, paresis
9  Paraplegia, hemiplegia, quadriplegia, lethargy, semicoma
10 Death Survival data are shown in Table 7 below. The mean survival for the dexamethasone group was 23.4 days, compared with 34.8 days in the M23F2G group and 25.5 days in the Hu23F2G group. No statistical significance could be assigned to the survival scores for the antibody treated animals compared to those of the dexamethasone treated animals, likely due to the potency of the BP preparation.

TABLE 7

SURVIVAL AFTER TREATMENT (DAYS)

| (Animal No.) Dexamethasone | | (Animal No.) M23F2G | | (Animal No.) Hu23F2G | |
| --- | --- | --- | --- | --- | --- |
| T89241 | 24 | T89341 | 42 | 91339 | 11 |
| 91444 | 8 | 91424 | 42 | F91307 | 42 |
| 91449 | 42 | 91425 | 6 | M91353 | 42 |
| 92144 | 42 | 92150 | 42 | 92136 | 7 |
| 92152 | 3 | 91331 | 42 | | |
| F91337 | 3 | | | | |
| F91304 | 42 | | | | |
| Mean | 23.4 | | 34.8 | | 25.5 |
| SD | ±18.7 | | ±16.1 | | ±19.1 |

Clinical score and lesion area were determined at onset of disease (±3 days) and ten days post treatment (±3 days), except for two animals in the dexamethasone group (92152 and F91337) that died three days after onset, and the post scan was obtained on the day of death. The values for each of the 3 treatment groups are shown in Table 8. Clinical score values shown in Table 8 were those obtained on the same day as the scan. There was no significant difference between clinical scores at onset of disease between the three treatment groups; however, statistically significant differences were noted post-treatment in both clinical score and lesion area. [1-p for clinical scores, onset versus post; Dex=0.73, M23F2G=0.004, Hu23F2G=0.0001; 1-p for lesion area, onset versus post, Dex=0.27, M23F2G=0.007, Hu23F2G =0.07].

TABLE 8

CLINICAL SCORE AND LESION AREA VALUES

| | Clinical Score | | | Lesion Area | | |
| --- | --- | --- | --- | --- | --- | --- |
| Animal (Dex) | Onset | Post (d10+3) | % change | Onset | Post (d10+3) | % change |
| T89241 | 7 | 2 | −71.4 | 5237 | 3512 | −33 |
| 91444 | 4 | 5 | +25.0 | 8441 | 6607 | −22 |
| 91449 | 7 | 7 | 0 | 2514 | 3315 | +32 |
| 92144 | 4 | 4 | 0 | 7916 | 5575 | −30 |
| 92152 | 4 | 9 | +125 | 9209 | 12904 | +40 |
| F91337 | 7 | 9 | +28 | 4566 | 3566 | −22 |
| F91304 | 8 | 8 | 0 | 10135 | 4342 | −57 |
| Mean | 5.86 | 6.29 | +15.2% | 6860 | 5688 | −13.1% |
| SD | ±1.77 | ±2.69 | | ±2788 | ±3406 | |
| (M23F2G) | | | | | | |
| T89341 | 7 | 0 | −100 | 1853 | 0 | −100 |
| 91424 | 6 | 5 | −16.7 | 10998 | 0 | −100 |
| 91425 | 4 | 4 | 0 | 7107 | 845 | −88 |
| 92150 | 4 | 0 | −100 | 499 | 151 | −70 |
| 91331 | 6 | 0 | −100 | 6237 | 269 | −96 |
| Mean | 5.4 | 1.8 | −63.3% | 5339 | 253 | −90.8% |
| SD | ±1.34 | ±2.49 | | ±4229 | ±350 | |
| (Hu23F2G) | | | | | | |
| 91339 | 5 | 2 | −60 | 3773 | 569 | −85 |
| F91307 | 9 | 2 | −77.8 | 6855 | 230 | −97 |
| M91353 | 6 | 0 | −100 | 14870 | 4219 | −72 |
| 92136 | 6 | 3 | −50 | 20268 | 9344 | −54 |
| Mean | 6.5 | 1.75 | −71.95% | 11441.5 | 3591 | −77% |
| SD | ±1.73 | ±1.26 | | ±7517 | ±4240 | |

In summary, M23F2G and Hu23F2G have the same beneficial effect on monkey EAE as antibody 60.3 in terms of survival. Analyses of clinical severity and MRI endpoints also supports a beneficial effect of M23F2G and Hu23F2G compared to dexamethasone alone in monkey EAE.

The foregoing examples describe a method for treatment for inhibiting inflammatory processes and alleviating symptoms associated with inflammatory disease states by administering a reagent, such as an antibody, that blocks leukocyte adhesion and migration to inflammatory sites. While the present invention has been described in terms of specific methods and compositions, it is understood that variations and modifications will occur to those skilled in the art upon consideration of the description of the present invention. As one example, while two anti-CD18 mAbs, 60.3 and 23F2G, have been demonstrated to be useful in practice of methods of the invention, it is expected that any antibody which competes with mAb 60.3 and/or with 23F2G for binding to LFA-1 will also be useful, whether or not such antibody recognizes on epitope present on CD18. Accordingly, it is intended in the appended claims to cover all such equivalent variations which come within the scope of the invention as claimed.

What is claimed is:

1. Hybridoma cell line 23F2G, A.T.C.C. HB 11801.
2. Monoclonal antibody 23F2G produced by hybridoma cell line 23F2G, A.T.C.C 11081.
3. CHO cell line 6E6, A.T.C.C. CRL11398.
4. Monoclonal antibody 6E6 produced by CHO cell line 6E6, A.T.C.C. CRL11398.
5. CHO cell line B13–24, A.T.C.C. CRL11397.
6. Monoclonal antibody B13–24 produced by CHO cell line B13–24, A.T.C.C. CRL11397.

* * * * *

UNITED STATES PATENT AND TRADEMARK OFFICE
CERTIFICATE OF CORRECTION

PATENT NO. : 5,854,070
DATED : December 29, 1998
INVENTOR(S) : Lynn M. Rose

It is certified that error appears in the above-identified patent and that said Letters Patent is hereby corrected as shown below:

Column 2, line 13 replace "(1987)." with --(1987)].;

Column 3, line 13 replace "FMLP" with --fMLP--;

Column 7, line 26 replace "89070" with --89070--;

Column 7, line 27 replace "89075" with --89075--;

Column 7, line 28 replace "89080" with --89080--;

Column 7, line 29 replace "89069" with --89069--;

Column 7, line 30 replace "89071" with --89071--;

Column 7, line 31 replace "89074" with --89074--;

UNITED STATES PATENT AND TRADEMARK OFFICE
CERTIFICATE OF CORRECTION

PATENT NO. : 5,854,070

DATED : December 29, 1998

INVENTOR(S) : Lynn M. Rose

It is certified that error appears in the above-identified patent and that said Letters Patent is hereby corrected as shown below:

Column 7, line 34 replace "89077" with --89077--;

Column 7, line 36 replace "89069" with --89069--;

Column 7, line 40 replace "86187" with --89167--;

Column 7, line 41 replace "86209" with --86209--;

Column 13, line 59 replace "the" with --The--;

Column 19, line 34 replace "77.-4216" with --77:4216--

Column 20, line 4 replace "with increasing" with --with an increasing--;

Signed and Sealed this

Seventh Day of December, 1999

Attest:

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

CGATACGAAT TCAGGTSMAR CTGCAGSAGT CWG    33

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

GCTATCGGAT CCGGARCCAG TTGTAYCTCC ACACAC    36

( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

CGATACGAAT TCGATRTTKT GATGACYCAR RCTSCA    36

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

GCTATCGGAT CCACTGGATG GTGGGAAGAT GGA    33

( 2 ) INFORMATION FOR SEQ ID NO:5:

( i ) SEQUENCE CHARACTERISTICS:
        ( A ) LENGTH: 339 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS (B) LOCATION: 1..339

(xi) SEQUENCE DESCRIPTION: SEQ ID NO:5:

| | | | | | | | | | | | | | | | | |
|---|---|---|---|---|---|---|---|---|---|---|---|---|---|---|---|---|
| GGG | GCT | GAA | CTG | GCA | AGA | CCT | GGG | ACT | TCA | GTG | AAG | TTG | TCC | TGC | AAG | 48 |
| Gly | Ala | Glu | Leu | Ala | Arg | Pro | Gly | Thr | Ser | Val | Lys | Leu | Ser | Cys | Lys | |
| 1 | | | | 5 | | | | | 10 | | | | | 15 | | |
| GCC | TCT | GGC | TAC | ACC | TTT | ACT | AAT | AAT | TGG | ATG | CAG | TGG | ATA | AAA | CAG | 96 |
| Ala | Ser | Gly | Tyr | Thr | Phe | Thr | Asn | Asn | Trp | Met | Gln | Trp | Ile | Lys | Gln | |
| | | | 20 | | | | | 25 | | | | | 30 | | | |
| AGG | CCT | GGA | CAG | GGT | CTG | GAA | TGG | ATT | GGG | GCT | ATT | TTT | CCT | GGA | GAT | 144 |
| Arg | Pro | Gly | Gln | Gly | Leu | Glu | Trp | Ile | Gly | Ala | Ile | Phe | Pro | Gly | Asp | |
| | | 35 | | | | | 40 | | | | | 45 | | | | |
| GAC | GAG | ACT | AGA | TAC | ACT | CAG | AAA | TTC | AGG | GGC | AAG | GCC | ACA | TTG | ACT | 192 |
| Asp | Glu | Thr | Arg | Tyr | Thr | Gln | Lys | Phe | Arg | Gly | Lys | Ala | Thr | Leu | Thr | |
| | 50 | | | | | 55 | | | | | 60 | | | | | |
| GCA | GAT | AAG | TCC | TCC | AAT | ACA | GGT | TAC | TTG | CAG | CTC | AGC | AGC | TTG | ACA | 240 |
| Ala | Asp | Lys | Ser | Ser | Asn | Thr | Gly | Tyr | Leu | Gln | Leu | Ser | Ser | Leu | Thr | |
| 65 | | | | | 70 | | | | | 75 | | | | | 80 | |
| TCT | GAA | GAC | TCT | GCG | GTC | TAT | TAT | TGT | GGA | AGA | GGG | GGA | AAA | TTA | CGA | 288 |
| Ser | Glu | Asp | Ser | Ala | Val | Tyr | Tyr | Cys | Gly | Arg | Gly | Gly | Lys | Leu | Arg | |
| | | | | 85 | | | | | 90 | | | | | 95 | | |
| CCC | TTT | GCT | TTG | GAC | TAC | TGG | GGT | CAA | GGA | GCT | TCA | GTC | ATC | GTC | TCC | 336 |
| Pro | Phe | Ala | Leu | Asp | Tyr | Trp | Gly | Gln | Gly | Ala | Ser | Val | Ile | Val | Ser | |
| | | | 100 | | | | | 105 | | | | | 110 | | | |
| TCA | | | | | | | | | | | | | | | | 339 |
| Ser | | | | | | | | | | | | | | | | |

(2) INFORMATION FOR SEQ ID NO:6:

(i) SEQUENCE CHARACTERISTICS:
        (A) LENGTH: 309 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..309

(xi) SEQUENCE DESCRIPTION: SEQ ID NO:6:

| | | | | | | | | | | | | | | | | |
|---|---|---|---|---|---|---|---|---|---|---|---|---|---|---|---|---|
| GCT | TCT | TTG | ACT | GTG | TCT | CTA | GGG | CAG | AGG | GCC | ACC | ATA | TCC | TGC | AGA | 48 |
| Ala | Ser | Leu | Thr | Val | Ser | Leu | Gly | Gln | Arg | Ala | Thr | Ile | Ser | Cys | Arg | |
| 1 | | | | 5 | | | | | 10 | | | | | 15 | | |
| GCC | AGT | GAA | AGC | GTT | GAA | AGT | TAT | GGC | AAT | AAT | TTT | ATG | TAC | TGG | TAT | 96 |
| Ala | Ser | Glu | Ser | Val | Glu | Ser | Tyr | Gly | Asn | Asn | Phe | Met | Tyr | Trp | Tyr | |
| | | | 20 | | | | | 25 | | | | | 30 | | | |
| CAA | CAG | AAA | CCG | GGA | CAT | CCA | CCC | AAA | CTC | CTC | ATC | TAT | CTT | GCA | TCC | 144 |
| Gln | Gln | Lys | Pro | Gly | His | Pro | Pro | Lys | Leu | Leu | Ile | Tyr | Leu | Ala | Ser | |
| | | 35 | | | | | 40 | | | | | 45 | | | | |
| AAC | CTA | GAA | TCT | GGA | ATC | CCT | GCC | AGG | TTC | AGT | GGC | AGT | GGG | TCT | GGG | 192 |
| Asn | Leu | Glu | Ser | Gly | Ile | Pro | Ala | Arg | Phe | Ser | Gly | Ser | Gly | Ser | Gly | |
| | 50 | | | | | 55 | | | | | 60 | | | | | |
| ACA | GAC | TTC | ACC | CTC | ACC | ATT | GAT | CCT | GTG | GAG | ACT | GAT | GAT | GCT | GCA | 240 |
| Thr | Asp | Phe | Thr | Leu | Thr | Ile | Asp | Pro | Val | Glu | Thr | Asp | Asp | Ala | Ala | |
| 65 | | | | | 70 | | | | | 75 | | | | | 80 | |
| ACC | TAT | TAC | TGT | CAC | CAA | GAT | AAT | GAG | GAT | CCT | CCG | ACG | TTC | GGT | GGA | 288 |
| Thr | Tyr | Tyr | Cys | His | Gln | Asp | Asn | Glu | Asp | Pro | Pro | Thr | Phe | Gly | Gly | |
| | | | | 85 | | | | | 90 | | | | | 95 | | |
| GGC | ACC | AAG | CTG | GAA | TTC | AAA | | | | | | | | | | 309 |
| Gly | Thr | Lys | Leu | Glu | Phe | Lys | | | | | | | | | | |
| | | | 100 | | | | | | | | | | | | | |

( 2 ) INFORMATION FOR SEQ ID NO:7:

( i ) SEQUENCE CHARACTERISTICS:
        ( A ) LENGTH: 360 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..360

( x i ) SEQUENCE DESCRIPTION: SEQ ID NO:7:

```
CAG  GTG  CAG  CTG  GTG  CAG  TCT  GGG  GCT  GAG  GTG  AAG  AAG  CCT  GGG  GCT      48
Gln  Val  Gln  Leu  Val  Gln  Ser  Gly  Ala  Glu  Val  Lys  Lys  Pro  Gly  Ala
 1                   5                  10                       15

AGC  GTG  AAG  GTC  TCC  TGC  AAG  GCT  TCT  GGA  TAC  ACC  TTC  ACT  AAT  AAT      96
Ser  Val  Lys  Val  Ser  Cys  Lys  Ala  Ser  Gly  Tyr  Thr  Phe  Thr  Asn  Asn
                 20                      25                      30

TGG  ATG  CAG  TGG  GTG  CGA  CAG  GCC  CCT  GGA  CAA  GGG  CTC  GAG  TGG  ATG     144
Trp  Met  Gln  Trp  Val  Arg  Gln  Ala  Pro  Gly  Gln  Gly  Leu  Glu  Trp  Met
             35                      40                      45

GGA  GCT  ATT  TTT  CCT  GGA  GAT  GAC  GAG  ACT  AGA  TAC  ACT  CAG  AAA  TTC     192
Gly  Ala  Ile  Phe  Pro  Gly  Asp  Asp  Glu  Thr  Arg  Tyr  Thr  Gln  Lys  Phe
         50                      55                      60

AGG  GGC  AAG  GCT  ACC  ATT  ACC  GCG  GAC  ACA  TCC  ACG  AGC  ACA  GCC  TAC     240
Arg  Gly  Lys  Ala  Thr  Ile  Thr  Ala  Asp  Thr  Ser  Thr  Ser  Thr  Ala  Tyr
 65                      70                      75                      80

ATG  GAG  CTG  AGC  AGC  CTG  AGA  TCT  GAG  GAC  ACG  GCC  GTG  TAT  TAC  TGT     288
Met  Glu  Leu  Ser  Ser  Leu  Arg  Ser  Glu  Asp  Thr  Ala  Val  Tyr  Tyr  Cys
                         85                      90                      95

GGC  AGA  GGG  GGA  AAA  TTA  CGA  CCC  TTT  GCT  TTG  GAC  TAC  TGG  GGC  CAA     336
Gly  Arg  Gly  Gly  Lys  Leu  Arg  Pro  Phe  Ala  Leu  Asp  Tyr  Trp  Gly  Gln
                 100                     105                     110

GGA  ACC  CTG  GTC  ACC  GTC  TCC  TCA                                             360
Gly  Thr  Leu  Val  Thr  Val  Ser  Ser
             115                     120
```

( 2 ) INFORMATION FOR SEQ ID NO:8:

( i ) SEQUENCE CHARACTERISTICS:
        ( A ) LENGTH: 333 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..333

( x i ) SEQUENCE DESCRIPTION: SEQ ID NO:8:

```
GAC  ATC  CAG  ATG  ACC  CAG  TCT  CCA  TCC  TCC  CTG  TCT  GCA  TCT  GTA  GGA      48
Asp  Ile  Gln  Met  Thr  Gln  Ser  Pro  Ser  Ser  Leu  Ser  Ala  Ser  Val  Gly
 1                   5                  10                       15

GAC  AGA  GTC  ACC  ATC  ACT  TGC  AGA  GCC  AGT  GAA  AGC  GTT  GAA  AGT  TAT      96
Asp  Arg  Val  Thr  Ile  Thr  Cys  Arg  Ala  Ser  Glu  Ser  Val  Glu  Ser  Tyr
                 20                      25                      30

GGC  AAT  AAT  TTT  ATG  TAC  TGG  TAC  CAA  CAG  AAA  CCA  GGG  AAA  GCC  CCT     144
Gly  Asn  Asn  Phe  Met  Tyr  Trp  Tyr  Gln  Gln  Lys  Pro  Gly  Lys  Ala  Pro
             35                      40                      45

AAG  CTC  CTG  ATC  TAT  CTT  GCA  TCC  AAC  CTA  GAA  TCT  GGG  GTC  CCA  TCA     192
Lys  Leu  Leu  Ile  Tyr  Leu  Ala  Ser  Asn  Leu  Glu  Ser  Gly  Val  Pro  Ser
```

```
                  50                         55                          60
AGG  TTC  AGT  GGC  AGT  GGA  TCT  GGG  ACA  GAC  TTC  ACT  CTC  ACC  ATC  AGC      240
Arg  Phe  Ser  Gly  Ser  Gly  Ser  Gly  Thr  Asp  Phe  Thr  Leu  Thr  Ile  Ser
 65                      70                       75                       80

AGC  CTG  CAG  CCT  GAA  GAT  TTT  GCA  ACT  TAC  TAC  TGT  CAC  CAA  GAT  AAT      288
Ser  Leu  Gln  Pro  Glu  Asp  Phe  Ala  Thr  Tyr  Tyr  Cys  His  Gln  Asp  Asn
                     85                       90                       95

GAG  GAT  CCT  CCG  ACG  TTC  GGC  CAG  GGG  ACC  AAG  CTG  GAG  ATC  AAA           333
Glu  Asp  Pro  Pro  Thr  Phe  Gly  Gln  Gly  Thr  Lys  Leu  Glu  Ile  Lys
               100                      105                     110
```

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Asp  Ser  Asn  Leu  Trp  Asn
 1                     5
```